US011459564B2

(12) United States Patent
Rigo et al.

(10) Patent No.: US 11,459,564 B2
(45) Date of Patent: Oct. 4, 2022

(54) MODULATION OF FRATAXIN EXPRESSION

(71) Applicants: IONIS PHARMACEUTICALS, INC., Carlsbad, CA (US); BOARD OF REGENTS OF THE UNIVERSITY OF TEXAS SYSTEM, Austin, TX (US)

(72) Inventors: Frank Rigo, Carlsbad, CA (US); Thazha P. Prakash, Carlsbad, CA (US); David Corey, Dallas, TX (US)

(73) Assignees: IONIS PHARMACEUTICALS, INC., Carlsbad, CA (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/956,425

(22) PCT Filed: Dec. 21, 2018

(86) PCT No.: PCT/US2018/067087
§ 371 (c)(1),
(2) Date: Jun. 19, 2020

(87) PCT Pub. No.: WO2019/126641
PCT Pub. Date: Jun. 27, 2019

(65) Prior Publication Data
US 2021/0087559 A1 Mar. 25, 2021

Related U.S. Application Data

(60) Provisional application No. 62/609,056, filed on Dec. 21, 2017.

(51) Int. Cl.
*C12N 15/113* (2010.01)
(52) U.S. Cl.
CPC ...... *C12N 15/113* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/3341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |

(Continued)

FOREIGN PATENT DOCUMENTS

| | | | |
|---|---|---|---|
| WO | WO 2015/023937 | 2/2015 | |
| WO | WO-2016094374 A1 * | 6/2016 | ............. A61K 45/06 |

(Continued)

OTHER PUBLICATIONS

Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke, ST., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

(Continued)

*Primary Examiner* — Tracy Vivlemore
(74) *Attorney, Agent, or Firm* — Parker Highlander PLLC

(57) ABSTRACT

Certain embodiments are directed to methods and compounds for increasing FXN. Such methods and compounds are useful for increasing expression of FXN in cells and animals.

23 Claims, No Drawings
Specification includes a Sequence Listing.

(56) References Cited

U.S. PATENT DOCUMENTS

| | | |
|---|---|---|
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0184050 A1* | 7/2011 | De Kimpe ............ A61P 21/00 514/44 R |
| 2013/0130378 A1 | 5/2013 | Manoharan et al. |
| 2014/0107330 A1 | 4/2014 | Freier et al. |
| 2014/0128455 A1 | 5/2014 | Zain-Luqman et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |

(56) References Cited

U.S. PATENT DOCUMENTS

2015/0267195 A1 9/2015 Seth et al.
2015/0275212 A1 10/2015 Albaek et al.
2017/0166899 A1 6/2017 Prakash et al.

FOREIGN PATENT DOCUMENTS

WO WO 2017/186815 11/2017
WO WO 2019/126641 6/2019

OTHER PUBLICATIONS

Gautschi et al., "Activity of a novel bcl-2/bcl-xLbispecific antisense oligonucleotide against tumors of diverse histologic origins" J. Natl. Cancer Inst. (2001) 93:463-471.

International Search Report for PCT/US18/067087 dated Jul. 15, 2019.

Li et al., "Activation of Frataxin Protein Expression by Antisense Oligonucleotides Targeting the Mutant Expanded Repeat" Nucl Ac Ther (2018) 28: 23-33.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Shen et al., "Efficient electroporation of neuronal cells using synthetic oligonucleotides: identifying duplex RNA and antisense oligonucleotide activators of human frataxin expression" RNA (2019) 25: 1118-1129.

Shen et al., "Progress towards drug discovery for Friedreich's Ataxia: Identifying synthetic oligonucleotides that more potently activate expression of human frataxin protein" Bioorg Med Cehm (2020) 28: 1-8.

Shen et al., "Activating frataxin expression by single-stranded siRNAs targeting the GAA repeat expansion" Bioorg Med Chem Let (2018) 28: 2850-2855.

Woolf et al., "Specificity of antisense oligonucleotides in vivo" PNAS (1992) 89: 7305-7309.

* cited by examiner

SEQUENCE LISTING

<160> NUMBER OF SEQ ID NOS: 22

<210> SEQ ID NO 1
<211> LENGTH: 70000
<212> TYPE: DNA
<213> ORGANISM: Homo sapien

<400> SEQUENCE: 1
aacctgacag ctattaggat ctgcctactt gaggctaaaa gcaaccaaga gaggaacagc     60
tacagtgtac cacagagtcc ctcaacatct ttgcccacgc cacggtgccc cagcttctta    120

```
ccaagtgtgc ctgattcctc ttgactacct ccaaggaagt ggagaaagac aagttcttgc      180
gaagccttcg tcttctctga tatgctattc tatgtctatt tctttggcca aaaagatggg      240
gcaatgatat caactttgca gggagctgga gcatttgcta gtgacctttc tatgccagaa      300
cttgctaagc atgctagcta ataatgatgt agcacagggt gcggtggctc acgcctgtaa      360
tctcagcact ttgggcggcc gaggcgggcg gatcacctga ggtcaggagt tcgagaccag      420
cctggccaac atgatgaaac ccatctcta ctaaaaatac aaaaattagc caggcgtggt       480
ggtgggcacc tgcaatccca gctactctgg aggctgagac agaatctctt gaacccagga     540
ggtggagatt gcagtgagca gagatggcac cactgcattc cagcctgggc aacaaagcaa     600
gactctgtct caaataataa taataataat aactaatgat gcagctttct ctctctgagt     660
atataatgca gttctgatga tgtgaggaag gcctcactg ttggtgtggc agagtctgag      720
accatggctg gcaatgaaaa cactacccctt tgatgcctat gggctctccc tttatggttt    780
caaggagggc ttctcaatct tggcagaatt ttggactgga tagttctttg ttgcacaggt     840 gggggctgt cctgcacatc acaggatgtt tcatccctgg cctctaccta ctagatgcca      900
gtagaacata cccaccccac agctgcctgt tgtgacaatc aaaagcatct ccagatactt     960
tgcaggggga aaatgatttc tccaggcctg gcatatacat aacagtattt aagcagctgc    1020
ctagaattaa ttaaacacag aaggatgtct ctcatccaga atgccctgga ccacctcttt    1080
gataggcaat cagatcccac ctcctccacc ctattttga aggccctgtg ccaacaccac     1140
ttcttccatg aatacttcct tgattccccc atccctagct ctatataaat ctcccactca    1200
acactcacac ctgttagttt acattcctct tgacacttgt catttagcat cctaagtatg    1260
taaacatgtc tctcttcacg attcacaaag tggctttgga agaactttag taccttccca    1320
tcttctctgc catggaaagt gtacacaact gacatttct ttttttttaa gacagtatct     1380
tgctatgatg gccgggctgg aatgctgtgg ctattcacag gcacaatcat agctcactgc    1440
agccttgagc tcccaggctc aagtgatcct cccgcctcag cctcctgagt agctgagatc    1500
acaggcatgc actaccacac tcggctcaca tttgacatcc tctaaagcat atataaaatg    1560
tgaagaaaac tttcacaatt tgcatccctt tgtaatatgt aacagaaata aaattctctt    1620
ttaaaatcta tcaacaatag gcaaggcacg gtggctcacg cctgtcgtct cagcactttg    1680
tgaggcccag gcgggcagat cgtttgagcc tagaagttca agaccaccct gggcaacata    1740
gcgaaacccc ctttctacaa aaaatacaaa aactagctgg gtgtggtggt gcacacctgt    1800
agtcccagct acttggaagg ctgaaatggg aagactgctt gagcccggga gggagaagtt    1860
gcagtaagcc aggaccacac cactgcactc cagcctgggc aacagagtga gactctgtct    1920
caaacaaaca aataaatgag gcgggtggat cacgaggtca gtagatcgag accatcctgg    1980
ctaacacggt gaaacccgtc tctactaaaa aaaaaaaaa atacaaaaaa ttagccaggc    2040
atggtggcgg gcgcctgtag tcccagttac tcgggaggct gaggcaggag aatggcgtga    2100
aaccgggagg cagagcttgc agtgagccga gatcgcacca ctgccctcca gcctgggcga    2160
cagagcgaga ctccgtctca atcaatcaat caatcaataa aatctattaa caatatttat    2220
tgtgcactta acaggaacat gcccttgtcca aaaaaaactt tacagggctt aactcatttt    2280
atccttacca caatcctatg aagtaggaac ttttataaaa cgcatttat aaacaaggca     2340 cagagaggtt aattaacttg ccctctggtc acacagctag gaagtgggca gagtacagat    2400
ttacacaagg catccgtctc ctggccccac atacccaact gctgtaaacc cataccggcg    2460
```

```
gccaagcagc ctcaatttgt gcatgcaccc acttcccagc aagacagcag ctcccaagtt    2520
cctcctgttt agaattttag aagcggcggg ccaccaggct gcagtctccc ttgggtcagg    2580
ggtcctggtt gcactccgtg cttttgcacaa agcaggctct ccattttgt taaatgcacg    2640
aatagtgcta agctgggaag ttcttcctga ggtctaacct ctagctgctc ccccacagaa    2700
gagtgcctgc ggccagtggc caccagggt cgccgcagca cccagcgctg gagggcggag    2760
cgggcggcag acccggagca gcatgtggac tctcggcgc cgcgcagtag ccggcctcct    2820
ggcgtcaccc agcccagccc aggcccagac cctcacccgg gtcccgcggc cggcagagtt    2880
ggccccactc tgcggccgcc gtggcctgcg caccgacatc gatgcgacct gcacgccccg    2940
ccgcgcagta agtatccgcg ccgggaacag ccgcgggccg cacgccgcgg ccgcacgcc    3000
gcacgcctgc gcaggaggc gccgcgcacg ccggggtcgc tccgggtacg cgcgctggac    3060
tagctcaccc cgctccttct cagggcggcc cggcggaagc ggccttgcaa ctcccttctc    3120
tggttctccc ggttgcattt acactggctt ctgctttccg aaggaaaagg ggacattttg    3180
tcctgcggtg cgactgcggg tcaaggcacg ggcgaaggca gggcaggctg gtggagggga    3240
ccggttccga ggggtgtgcg gctgtctcca tgcttgtcac ttctctgcga taacttgttt    3300
cagtaatatt aatagatggt atctgctagt atatacacac acataatgtg tgtgtctgtg    3360
tgtatctgta tatagcgtgt gtgttgtgtg tgtgtgtttg cgcgcacggg cgcgcgcaca    3420
cctaatattt tcaaggctgg attttttga acgaaatgct ttcctggaac gaggtgaaac    3480
tttcagagct gcagaatagc tagagcagca ggggccctgg cttttggaaa ctgacccgac    3540
cttttattcca gattctgccc cactccgcag agctgtgtga ccttgggga ttcccctaac    3600
ctctctgaga cgtggctttg ttttctgtag ggagaagata aggtgacgc ccattttgcg    3660
gacctggtgt gaggattaaa tgggaataac atagataaag tcttcagaac ttcaaattag    3720
ttcccctttc ttcctttggg gggtacaaag aaatatctga cccagttacg ccacggcttg    3780
aaaggaggaa acccaaagaa tggctgtggg gatgaggaag attcctcaag gggaggacat    3840
ggtatttaat gagggtcttg aagatgccaa ggaagtggta gagggtgttt cacgaggagg    3900
gaaccgtctg ggcaaaggcc aggaaggcgg aaggggatcc cttcagagtg gctggtacgc    3960
cgcatgtatt aggggagatg aaagaggcag gccacgtcca agccatattt gtgttgctct    4020
ccggagtttg tactttaggc ttgaacttcc cacacgtgtt attggcccca cattgtgttt    4080
gaagaaactt tgggattggt tgccagtgct taaaagttag gacttagaaa atggatttcc    4140
tggcaggacg cggtggctca tgcccataat ctcagcactt tgggaggcct aggaaggtgg    4200
atcacctgag gtccggagtt caagactaac ctggccaaca tggtgaaacc cagtatctac    4260
taaaaaatac aaaaaaaaa aaaaagaag aagaagaaga agaaaataaa gaaaagttag    4320
ccgggcgtgg tgtcgcgcgc ctgtaatccc agctactcca gaggctgcgg caggagaatc    4380
gcttgagccc gggaggcaga ggttgcatta agccaagatc gcccaatgca ctccggcctg    4440
ggcgacagag caagactccg tctcaaaaaa taataataat aaataaaaat aaaaaataaa    4500
atggatttcc cagcatctct ggaaaaatag gcaagtgtgg ccatgatggt ccttagatct    4560
cctctaggaa agcagacatt tattacttgg cttctgtgca ctatctgagc tgccacgtat    4620
tgggcttcca ccctgcctg tgtggacagc atgggttgtc agcagagttg tgttttgttt    4680
tgttttttg agacagagtt tccctcttgt tgcccaggct ggagtgcagt ggctcagtct    4740
cagctcactg caacctctgc ctcctgggtt caagtgattc tcctgcctca gcctcccgag    4800
tagctgggat tatcggctaa ttttgtattt ttagtagaga cagatttctc catgttggtc    4860
```

```
aggctggtct cgaactccca acctcaggtg atccgccac ctcgccctcc caaagtgctg    4920
gaattacagg cgtgagccac cgcgtctggc catcagcaga gttttttaatt taggagaatg    4980 acaagaggtg gtacagtttt ttagatggta cctggtggct gttaagggct attgactgac    5040
aaacacaccc aacttggcgc tgccgcccag gaggtgaca ctgggtttct ggatagatgg    5100
ttagcaacct ctgtcaccag ctgggcctct ttttttctat actgaattaa tcacatttgt    5160
ttaacctgtc tgttccatag ttcccttgca catcttgggt atttgaggag ttgggtgggt    5220
ggcagtggca actggggcca ccatcctgtt taattatttt aaagccctga ctgtcctgga    5280
ttgaccctaa gctcccctg gtctccaaaa ttcatcagaa actgagttca cttgaaggcc    5340
tcttccccac ccttttctcc acccttgca tctacttcta aagcagctgt caacagaaa    5400 cagaatggga gccacacaca taattctaca ttttctagtt aaaagaaaa aaaaatcatt    5460 ttcaacaata tatttattca acctagtaca tacaaaatat tatcattcca acatgtaatc    5520
agtattttaa aaatcagtaa tgagaccagg cacggtggct cacgactgta atcccaggac    5580
tttgggaggc cgaggcgagt ggatcatctg agatcaggag ttcaagacca gcctggccaa    5640
catggtgaaa ccccatctct actaaaaact agctcagcat ggtggtgggt gcctgtagtc    5700
ccagctactc gggaggctga ggcatgagaa tcacttgagc ccaggaggca gaggttgcag    5760
tgagccaaga ttttggggga ttctgtgaca tacaaaaaaa atcagtaata agatatcttg    5820
catactcttt tcgtactcat atacttccag catatctcaa ttcacaattt ctaagtaaat    5880
gctctatctg tatttacttt tataaaattc acaattaaaa atgaaggttc acatagtcaa    5940
gttgttccaa acacacttaa atgtctccta ggctgggtgt ggttgctcac acctgtaatc    6000
ccagcacttt gggaggctga gatgggcgga tcacctgagg tcaggagttt gagaccagcc    6060
tggccaacat ggtgaaaccc cgtctctact aaaaatacaa aaattagctg gatgtggtgg    6120
cactcacctg taatcccagc tactcaggag gctgaggcag gataattgct tgaacccggg    6180
aggtggtgga ggttgcagtg agccgagatc gcaccactgc cttccaacct gggcgacaga    6240
gcgagactcc gtctcaaaaa aaaaaaaag ctcctaata actttattac tttattatca    6300
cctcaaataa ttaaaattaa atgaagttga aaatccaggt cctcagtccc attagccaca    6360
tttctagtgc tcagtagcca cggggctgg tgaccaccac atgggacagc atatttagta    6420
cctgatcatt ggttctcaga tctggctact cagcagaacc aagaatccac agaaacggct    6480
tttaaaagca cagccccaca gcccccagcc ccagccttac ctacctggag gctgggaagg    6540
actctgattc cacgaggcag cctatgtttt ttgatggagg gatgtgacag gggctgcatc    6600
tttaacgttt cctcttaaat actggagaca gcttcgagga ggagataact ggatgtgtct    6660
tagtccattt gatggaggga tgtgacgggg ctgcgtcttt aacgtttcct cttaaatacc    6720
ggagacagct tcgagaagga gataactgga tgtttcttag tccatttct gttgcttgtg    6780 acagaatacc tgaaactggg caatttatat ggtaaaaaat ttcttcctta ctgctctgga    6840
ggctgagaag tccaaagtca agtcccttct tgctggtggg actttgcag agtattgagg    6900 cggcaccggg cgtcatatgg taaggggctg agtgtgctac ctcaggtgtc ttttctttt    6960 cttataaagc ctaactagtt tcactcccat gataacccat taatctatga atggattaat    7020
ccattattga gggaagaacc ttcatgaccc agtcaccgct taaaggcccc acctctcaat    7080
actgccacat cgggaattaa gtttcaacat gagtttcgga ggtgacaaac attcaaacca    7140
tagcatgctg tctcttaaat gactcaataa gctcctgtgg catccacttc tgcatgcctt    7200
```

```
gggcagcttt tagacatctg tccatttcc tagagggaca agaccaccac ctgtgatcct    7260
atgaccttt ggctttaggc ctaacaagca ggttataccc tcactcactt tcaaatcatt    7320
tttattgtct tgcagacaat ttacacaagt ttacacatag aaaaggatat gtaaatattt    7380
atacgctgcc gggcgcggtg gctcacgcct gtaatcccag cactttggga ggccgaggca    7440
ggtggatcac gagttcagga gatggagacc atcctggcta atacgatgaa accccatctc    7500
tactaaaaat acaaaaaatt agccgggcgt ggtgacgggt gcctgtagtc cccactactc    7560
gggacgctga ggcaggagaa tggcgtgaac ccgggaggca gagcttgcag tgatccgaga    7620
tcgtgccact gcactccagc ctgggtgaca gagcgagact gcatctcaaa gaaaaaaata    7680
aataaataaa taaatattta tactgcttat aaactaataa taaatgctat ggtctgcatg    7740
tttgtgtcac cccaccattc atatgttaaa acctaatcac caaagtgata ttaggaggtg    7800
gggcccttgg gaggtgatga ggtatgaggg tggagcccat atgattggga ttagtgccct    7860
tctaaaatag cccaacggag cccagtgaca aggcatcatc tatgaaccag gaaactggcc    7920
ctcaccagac accaaagctg ttggtgcatt gatcttggat ttcccaccct ccaggactct    7980
aagaaacaca tttctattgt ttataagcca cccagtggct ggtattttgt tataacatcc    8040
cagactaaga caaataacaa atacttgtat ccctgacacc aggttaagag atagaatttg    8100
tttgttcctc tggaggccct tgtcttcacc ccatcactgc cctgtcctcc ctggaggaat    8160
ctgccagccc gaattctgtt catcgtaccc tccttttctt agagtttgac ctcctctgta    8220
tctcccccaa tccatgtatt gcttatatac aaggtattct gctgtatctg ttctgctatg    8280
gcttgcccct tttgttcaac actgttttg tgcgtcatct gcattgatgc atgcagttgt    8340
cctttatttg ttctcactgc tggatagtat ctggttgggt aaatatatca cactgtaaat    8400
cacactatcc aggttccttt aggtgacatt tggttgattg cagtgttctg ttgttacgat    8460
ggtgctgctg tgactgttct tgtgcatgga cagaagttcc tttcaggtga atttctcaga    8520
atggaattgc tgggcaaagg ggcagccaat aatcaactca tttgatgcca aaagtggtgg    8580
tgccagttca tcctcccctg cgaggtatgg gtcctgattc actcttcaag tgctgtggtt    8640
tgacagggcc gggggtgaca aggggacacc tgggaaggaa agctgggctc cctgctggcc    8700
atccaggcca gtccttacca gggggtaggc aatgattggg tcaagtggtt cctgaccact    8760
gggcctgaga cttcaggccc agaaactatc taatatttcc tcaaatgcat cccatgagca    8820
ggcactgtgt gagtgagcac acacatctga agcctcaagc taggcaagcc taccatgact    8880
tgtggtccaa gggctcacgg gtgacctgga gttagaggga gacatggctg ccaggtggct    8940
ttagaaagaa cactcatcat ggccaggtgc ggtggcttac gcctgtaatc ccagcacttt    9000
gggaggccaa ggtgggtgga tcatgaggtc aggagtgaga ccagcctgac caacatgctg    9060
aaacctgtct ctcctaaaaa cacaaaaatt agctgggcat ggaggtgcac gcctgtaatc    9120
ccagctactc aggaggctga ggcaggagaa tcacttgaac ccgggaggcg gaggttgcaa    9180
taagcctaga ttgtgccact gcattccagc ctgggcaaca gagcaagact ccgtctcaga    9240
aaaaaaaaaa aaaggaaga acactcatcc tatgaccttg acctccaagc tttgcctccc    9300
tcaagcagaa cagaatggag cctcccttag gcagaggcgg aagtttgcct ctcacctagt    9360
tctccattct tttgttcaga gcctgaatac cctcaggctc tgtacttggg gtatttctgt    9420
tctcttgttt tatgctcacg gttgtgaggt tgttgtgag taccacgatc ccttccttca    9480
gaggagtaaa ctgaggttcc aaaaggttta gcagttgccc gaggaatatt aaattggcaa    9540
aagcaggtag aatataaagc aaggagtatt tggcaacggt tcttttttat gattaaaaac    9600
```

```
agccgaagaa agacttctac ttgtgccttt gaaggagtaa ctgcatttga ccttcccacc    9660
agtaacaacc atcaaatctc tattaaatta aacacacaca cacacaaaca aaaacagcta    9720
ttgtgaaggt atcagcgact aagacaacta aggtttgagg ggccaggatc ctggagagat    9780
ggaaacttcc ctgaggtgag ccccacattc tcagacactt ttccttggat gttttgagca    9840
ctgctttaat tcctgggaaa acaattcctt ccactgtgca cagactctgg ggccagacag    9900
cttgggttca atcccagctc tgccacttaa tgtctgtgta tctgtgtagg caagttaccc    9960
tttggtgcgt cagtttcctc atctgtaaaa cacaactata gttgatcctc attcgttaag   10020
agtctgtact tgttaatttg ctcacttgct aaaatttgtt accccaaaat cagtacccct   10080
agccttttgg ggtcgtttca aagatgtgtg cagagcggca aaaaaatgtg agctcctcca   10140
ggctcatgtt cccagccaag gtccaacaaa gtgctgccct gccttcttat ttcagctgtc   10200
atagtgtaaa ctgtgtcctt ttcacagtct gattagtgcc atgttttca gattttatg    10260 ctttttctt ggttatttct ctgttaaaat tgtctccaag tgtagtgcaa agtttagcac    10320
gaggaggctg tgatgttcct tacagagaaa atgcatgtgt tagagaagct tgtcaggca    10380 tgagttaagg tgctgttgtc ctgagatcaa ttaatttgtt gttgttgttg tttgagacag   10440
ggtctccctc tgttgcccag gctgctggag tgcaatggtg taatcatagc tcactgcagc   10500
ctctacctct ctggctcaag caatcctccc acctcggcct cctgagtagc tgggactaca   10560
ggtacacccc accacaccca gataatgttt ttgatatttt tttaggtgga attttgctca   10620
tcacccaggc tggagtgcaa tggtgcgatc ctggctcact gcaacctcca cctcccggat   10680
tcaagcaatt cttctgcctc agcctcctga gtagcacaga ttacaggcac atgtcatcac   10740
gccttgctaa ttttgtgtt tttagtagag gcggggtttc accatgttgg ccaggctagt   10800
cttgaactcc tgacctcagg tgatccaccc gcctccgcct cccaaactgc agagattata   10860
ggcacgaacc acaatgcccg gcctcatgtt ttttattttt caagttgaaa tgaggtctct   10920
ctatgttgcc caggttggtc tcaaactctt gagctcaagt aatcctccca ccttggcctc   10980
ccaaagtgcg gggattacag gtgtgagcta ccatgcccag ccaagatcag tgttaatgaa   11040
tcaactatat atattacata aggtgtcttt aaacagaaat aaggttatat attgatcgat   11100
tggtaacaat gttgtgacca gcagcttaca gggtacctag ccttgtattt ctcctataaa   11160
taatttgctc gttgagtgtt tgtggcaact ttgtagcaca taactaccaa gaataaggac   11220
tgtaataaga gtacgtccct cacaggattg taatgaagac tgagtccatt tacataaagg   11280
ctgagagcag tgtcaagcag atggagaaca ctgtagaatg tgcgatagct ctaacagtgg   11340
ttatcatggc tgccctctca cttcttcaga gacatgtgtt tctaaggtct gcactctgcc   11400
ccaccctccc catccactgt cccccagccc gtttcctcct ccacttactt cccagccctg   11460
tgccttctgc cttctctttt ctgagtttgc taagggcact gctggctcaa gagcagtaac   11520
taacagtctc tcgcctcttc tctccatggc aaccagtgac ctttggagaa tgtaaacctt   11580
atcaccaatc tcttaaagcc cttcggtgcc ttcccaggat gacgtccagc tgaggtcctt   11640
ggcaagaccc agggcgcccc ctcctcgctc catcacctcc cctgtcacct cccctgcatc   11700
tccctactcc agctgcacca ctcttgtgcc ccagtggctc ttgtctgatt atttccttca   11760
tctccccagc tggtcagcag agctggtggt aatcaactca gaccctgtca cctggatgtc   11820
cagcagttag ggactaaaaa aaatcaacag gtcacattct gtcctgcaga tcatgataat   11880
aagatctgtc agacagcagt cagcagtcag agccaaatct tctggacttc agcaggattc   11940
```

```
tgcctcttgc tatttcctgt tgcctctctt agtgaccttt taagagcatt gtggatgcct    12000
cccagcctcc tgctaaccac cctgtaacct gaacagcctg cagcagccct gcccagtaga    12060
acttcctgat gtgatggaaa tgctgtgtct gcaccactag ccacatgtgg ccacaggatt    12120
ctcgaaactg gtggtgcagt tgaggagctg actttatatt ttatctcatt aaatttaaat    12180
gtaaatagct acgtgtggct tgttggctag cctattggaa aacacgggct tagagagaca    12240
cagggagaat cactgtaatg cactaaaaga aggtaaaaaa aaaaaaatcc taagaaatat    12300
tcctaaaata ctttaatata gggctgggtg cggtggctca catccagcat tttgggaagc    12360
tgaggagggc agatcacttg aggccaggag ttcaagacca gcctggccaa catggtgaaa    12420
ccccgtctct actaaaaata caaaaaatcg ggtgcggtgg cgggtgcctg taatcccagc    12480
tacgcgggag gctgaggcac gagaatcact cgaacccggg aggcggggt tgcagtgagc    12540 cgagatcgtg ccactgcact ccagcctggg cgacagagcg agacttcatc tcaaaaacaa    12600
aaaacaaaaa ccaaaaaaaa aaacttcagc atgattattt aaccaaaatg caggttagtt    12660
gttcaccgga tgcagagtcc aattaacaag agcaaggcct ggtaccaaaa aaagtgaatt    12720
tactccgaaa ctagcttggg tgaggggtac aaagcatcct gcctttcttt aaaagtgctg    12780
cttccccttg gaagtagaaa gtggacactt ttataaggta agggggaag tgtgcaaggg    12840 caagtggggg ggtccctctg ctagttccgt gcatactcta caggacagtt gacttggcac    12900
cttcctggtt agtaataagc tgtagcagtg gccaagtggg catgctttca gtatgccctc    12960
ccagtgaatg aaagtcctga ggcaaccccc aagggtggaa gtgccaggcc accaccact    13020 ggaggtgaaa gttccgtgat gggtttgctt tggtctgcga atctactgtc atgtggagag    13080
atctgtgctc tggaagagca tacagttaga aaagcttgcc ctgaagggaa tgtatggtga    13140
aggggaggtg aaaggttata tttgcatttc tgaagggcta agtaggaaac cgggaaccag    13200
gggagaggag aagagaagag aggataattt ttttttaagaa aagcaacata ttccctttt    13260 cttagaaaaa atggagcact cggttacagg cactcgaatg tagaagtagc aatatataaa    13320
ttatgcatta atgggttata attcactgaa aaatagtaac gtacttctta actttggctt    13380
tcagagttcg aaccaacgtg gcctcaacca gatttggaat gtcaaaaagc agagtgtcta    13440
tttgatgaat ttgaggaaat ctggaacttt gggccaccca gggtaagata aacaccttc    13500 cacgtcatag gtatcttcct ctctccttcc ctgcctctcc cattagaacc tggttttctt    13560
cctgagcagc aacaatctta ggcatctttc catgtgactg agtatccacc acattatttt    13620
taatgaaata gtattagatt gcatggatgt gacataatcc atttaaccca tcccctactg    13680
ttggacattc aggttgtttc cagagtttca atattatttt atttaatacc ctaatagtta    13740
gagcaggcca tgctgctatc acaaatagac ccaaatattt aatagctcaa accaataacg    13800
tttgtgtcct cctctctggg cagtacaggg ttggcatacc tcctgaagtg aattaggaac    13860
tacactcatt ccagcttcca gtttggtctt tatctgtcag tgccttactg tcctctgcat    13920
tgttgagtct cagtcacctt gtccaagttc cattggccag aaagggctag aagcacagaa    13980
gggctggaag tggcatttgt tcctcactca cattctggtg ggaagaactt agtggtgtgg    14040
ccttagctga ctgtaaggga ggctgggaaa tatagtctag cgagtgccct ggaaaaagcc    14100
ggcacggcat tccccatgga aagctgtcag gcacggctac agtctacccc ctgccaacca    14160
gtatctgcat ggaccctcct tccacactca gatgcattta cccccagccc caagagagcc    14220
aaccgatgcc catgtggtca ccacagccac ctccgagtcc aagatttcca ggtgacatgc    14280
agtctcctct ctcccagctt taggaatggc ttcttctgat ctacacacag acacagacac    14340
```

```
acacacacag acacacacac acacacacac acacacacac gatggagagg ggcaggataa    14400
ctgcaactgt aactccattc agaaaagagg cacagcacta gctgcccgca gcactggagc    14460
cctgctgggc agcactggat caacctctgc cctggcagag gagcatgttc ctccacaaat    14520
ccctgcttca gcctctcgag aggctcctcc ttgtctgtta ttttccttgg ccacaaggca    14580
ggcaggcagt gggaagtgtg ccctcctccg ggcaaggag ccttcacagc ccacttcctg     14640
ctaataacag tttggggttc cacagggtgt tttaagactc cagtcagcta ttttaggcca    14700
gactcatttc tctctctctc tctctttttt tttcttttat gaaatcacac cctgagaccc    14760
aggctggagt gcagtggtgc gatctcggct cactgcagcc tccgcctccc gggttcaagc    14820
aatcctcctg cctcagcctc ctgagtagct gggactatag gcgtgcagtg ccacacctag    14880 ctaattttg tattttagt aaagacgggg tttcaccatg ttggccaggc tggtcttgaa       14940
ctcctgacct cagatgatcc gcccgcctcg gcctcccaaa gtgctgggat tactggcatg    15000
agccactgcg cccagcccag actcattttt ctttgagagt aggcttttcc caaaagtagg    15060
cttctgagct attcactttc aggcagtccc atgtgccagg aaccacatcc aaatttcctc    15120
cgtggatggg agtctcaggc tgccttatct ccttgcatgt ccccatgccc agctgtctca    15180
gcctaagggc aggtaccttg aagtcaagtt aaacaataag attggagacc agcaatgccc    15240
tcagcctggt ttttgcagca ggactgagtc ccttgttttg gctcaatggg aagtctttgc    15300
tgttcaaagc cttagcttct ctggctgagt gcggtggctc acgcctgtca tcctagctct    15360
ttgggaggcc gaggtgagca gatcactgag gccaggagtt caagaccagc ctggccaaca    15420
tggtgaaacc ctgtctctac taaaaataca aaaagttagc caggcgtggt ggcaggcacc    15480
tgtaatccca gctactcggg agcctgaggc aggagaatcg cttaaaccca ggagatggag    15540
gctgcagtga gctgagatca tgccattgca ctccagcctg gtaacgagc gaaattccat     15600 ctctaaaaaa aagaaaaaaa aaaggcctta gattctccct ttgactttcc acgtttgtgc    15660 agcctttat ctccaatgct ccatttcatt ccatctcctg gcttattctt ttcttgtcac     15720
atctactaaa agcaacaaga agccaccggt attcaggaac attctacctg tccccagagc    15780
tatatgctca gtaggcatac agttggccct ccaggttatc tgagactcag atttccagag    15840
ggctttgcat ggctcacaag gtctgaagaa cctctgagcc tcccgcctgc ggtgtctgtt    15900
cattgacttt gccacagtct caaagaggca ctgcatgctg catgtttgag gttttgcttt    15960
tggtggcatc catttccagc ctcggcttcc ggcattcctc ccccagcaga ctctctgctg    16020
ctttccccct actccttctg gcagttctgg gaggttgcat agggcccttg caggatgccc    16080
caagtccagc tgcctctggc ctctgggaag cacaccttg acctgccatg tgtaggaaga     16140
cagcccgctt ctgccagggc caactctgc cggcaggtag caccttccaa cctcttcact     16200
ttggacttta taactgtcag gtataaagtc ggttgtgtcc ttacgtttct caaattcttc    16260
aagacacgtc aaccagcctc tcctacgcat tctctccagc tcagtctcaa acacaccct     16320 ttctctccag ctcactctca aaacacaccc tatcaggcca accactcttt ttaaaggaca    16380
gctcctcacc aatccagtca ggtagccttc cccacattgt atcctggaag tgggtgatgg    16440
actgggtggg gaagagggtc atatggcaaa tctgtatgtc ttacagtaat tgtctagcag    16500
cccctggtgt cttactttag gcccctgga aactttcaga tagtggagtt gtctgataca     16560
tatcttataa cctacagata ttaatatatc ctcacagggg cacaaaagct cttcaagga     16620 tgtttattat aataatattt ttattgttat aatttacatg ccataaaact aaccatttta    16680
```

```
aaatgtataa tgcaagggtt tttagtatat tcacaagatt gtgcagctgt cactactaat      16740
tccagaacat tttcattatt ccagaaggaa accctattca tattagcaat cactccccca      16800
ttccgccttt ccctaaaacc cagcaatcac taatctactt tctgtctctg tggatttaaa      16860
gtaattttaa atttgaaaaa tagtatctat aaggaaatgt atctagtcac aagcatacag      16920
cttgatgaat ttgtaaaaat tgaacagtcc tatgaacata ccctgtaagc tcaagacata      16980
gaatgttacc agcccctgca agcaagctgc ctgctcactt ctagtcatta acccctccct      17040
cttttccttc tagtcattaa cccttcagag taactattct gattaccaat agcatagatt      17100
agttctgcct gttgttttac tttatataaa ctgtctcatt aagtataaac atgtttgtgt      17160
atacttgtgt atttctttct atcacaatga tgtttgtgag attcatccat gctgttccta      17220
tagacaattc tattttgcag cgtagtattc cattgcatga ctataccaca atttatctgt      17280
gatattacaa aggaatactt gggcagtttc cagtttgggg ctataggata gttgtgatac      17340
aaatatttta gtatagtaca tgtcttttgg tgaacctggg tacacatttc tgttgtgtat      17400
accccttaag agtggagctg atgatcctgg ctaacaaggt gaaaccccgt ctctactaaa      17460
aatacaaaaa attagccggg cgtggtagcg ggcgcctgta gtcccagcta ctcgggaggc      17520
tgaggcagga gaatggcgtg aacccgggag gcggagcttg cttgcagtga gccgagatcg      17580
cgccactgca ctccagcctg ggcgacagag cgagactccg tctcaaaaaa aaaaaaaaa       17640 aaagagtgga gctgatgggt catagcatgt aaatgcattc aactttagta gatactgtcc      17700
aacagttttc caaagtgatt gtccaactta cttgcctatc agcagtatct gaaaagtcta      17760
gttgcttctt tcttggcca actcttttt ttttttgag atggagtttt gctcttgttg          17820
cccaggctgg agcgcaatgg cacgtcctct gctcactgca acctccgcct cctgggttca      17880
agcaattctc ctgcctcagc ctcccgagta gctgggatta caggcatgcg ccactatgcc      17940
cggctaattt tgtattttta gtagagacag ggtttctcca tgttggtcaa gctggtctcg      18000
aactcctaac ctcaggtgat ccgcccgcct cggcctcccg aagtgctggg attacaggca      18060
tgagccaccg cgccaggccg gccaactctt ttttatttta ttttatttta ctttaaagac      18120
agggtttcac tttgtcaccc aggatggaat gcaatggcac gatcacagct cactgcagcc      18180
ttgacctccc tggctcgggt gatccctccc acctcaggct cctgaggagc tagaactaca      18240
ggcatgggcc atgcccagct aattttttaa ttttggtag agacggggtc tctgttgtct       18300
cagattcctg ggttcaagtg atccttctcc cttggcctcc caaagttctg gtattacagg      18360
catgagccac tgcacccagc ccatggccag ctcttgatac gatctgtctc tttcttttct      18420
tttttttttt ttaatttgag aagtgttaaa taatctttct ttgatattat acataaacca      18480
caccaaaatg tctttcagta agtaaaatga accattttag atacagaaaa ttctaattag      18540
attggcatag ttaaggccaa aaatataaag ttgacattgc taccttatct tcagcccttg      18600
cctttaagag gcaaatgaac acaaaataca ggtgaatctt gcttggttct gagacagtga      18660
aggactttcc cccagtattt aaatatattt acataaccag ttacataaat ctaaatatta      18720
aaaaaatctc caatagattt tagatggcat tcaccatctt tgtgaaaagt tgaacattac      18780
taatgaaatc tgatcatatc tttagaagga taaacagtga tagcatttac tgaatcagaa      18840 taactgttt  ttgggtttt ctttgagacg gagttttgct cttgttgccc aggctggagt       18900
gcagtggtgc cacctcagct cactgcaacc tccgccccct ggattcaaga gattatcctg      18960
cctcagcctc ccgagtagct gggattacag gctcgcccca ccatgccag ctaattttg        19020 tattttagt agaggcgagg tttcaccatg tcagccaggc tggtcttgaa ctcctgacct       19080
```

```
caggtgatcc acccgcctca gcctcccaaa atgctaggat tacaggcgtg agccaccagg   19140
cccagcctat tttttttttt tttcttttt  tgagacggag tctcactctg tcacccaggc   19200
tggagtgcag tggcacaatg tcagctcatt gcaacctcca cctccggggt tcagtgatt    19260
ctcctgtctc agcctcccaa gtagctggga actacaggcg tgcaccacaa gcccagctaa   19320
tttttgtatt tttagtagag acagggtttt gccatattgg cctggctagt ttcaaactcc   19380
tgacctcagg tgagccacct acctcggcct ccgaaagtcc tgggattaca gacgtgagcc   19440
actgcactgc ctggcccaga aaggactatt aattgtagtt gcctctggga atgggggctg   19500
cctgcttctt tctgtaaccc cttctgtgct gtttaaattt tttttttttt tttttttttt   19560
gagacagagt ctcgctctgt cgcccaggct ggagtgcagt ggcgcaatct cggctcactg   19620
caagctccgc ctcccaggtt cacgccattc tcctgcctca gcctcctgag tagctgggac   19680
tacaggcacc cgtcaccacg cccggctaat ttttttgtatt ttcagtagag acggggtttc   19740
accatgttag ccaggatggt ctcgatctcc tgaccgtgtt atctgcctgc ctcggcctcc   19800
cagagtgctg ggattacagg catgagctac cacgcccggc ctttaaattt ttactttggg   19860
ccgggcacgg tgccttacgc ctgtaatcct aacatttcga gaagctgagg cacgtggtgg   19920
atcacttgat gtcacgagtt cagaccagcc actgcactcc agcctgggtg acagagtgag   19980
actctgtctc aaaaaaaaaa aaaaagaaa  gaaaaacttt tactttttac atgttatttt    20040
catcaattta atgaatttaa ataacaaatg tataaatttg atattaataa aatggaagca   20100
tttggtaatc atgttttggg ttttgtgctt cctctgcagc tctctagatg agaccaccta   20160
tgaaagacta gcagaggaaa cgctggactc tttagcagag ttttttgaag accttgcaga   20220
caagccatac acgtttgagg actatgatgt ctcctttggg gtacctcttg acttcttta    20280
tttttctgtt tcccctctta agaatttag  ttcactaaaa tgaagaattt ccctccagca   20340
gagctaagca tcaagtagca tgtagttgta ggtaggatta aaagactagg gttccgggag   20400
gtgaaggttg cagtgagcca aaatcacgcc actgcactcc agcctgggtg acagagcgag   20460
actctgtcat agatggatgg atggatggat ggatggatgg atggatggat agatagatag   20520
atagatagat agatagctgg atagatagat aagatagata agacaagact aggcttcaag   20580
ctgcagtcca gctctaccag gcttgttgtg actctgggca agtcactcag cctctctgag   20640
cctcattttc cagcttcagt ggatacccat gaaggcaaat cagagagggg cctgagtgtg   20700
tatttgtcca gcaggcagat ggagggaaca acaaactaga cccgtagttc ttcagtaggg   20760
ataagataac tgcccaaaag ttatttagat tacaaagact tgagccctgc tcctgtgaga   20820
cagtgatggg gtaggtcggg tgcattcctg ggaagcatat ttttgaaaag ctcacctggg   20880
attctaatgt gtatccctag gtcttattcc tagagatttt gattacttgg tctggggtgt   20940
ggcatgacct gggcagggca ctgggatttt taagctccac agatgattcc aatatgcagc   21000
tagtatgaga acttgttttt ttttgaagga gtctcactct gtcacccagg ctggagtgca   21060
gtggcgcaat ctcggctcac tgctccgctt cctgggttca agcagttctc ctgcctcagc   21120
ctcccgagta gctgggatta taggcatctg ccaccatgcc cagctaattt ttgcatttta   21180
gtaaagacgg ggtttcacca tgttggttag gctggtctcg atctcctgac ctcaaatggt   21240
ccaccccccat cagccttcca aagttttggg ataacaggcg tgagccacca ggtccggcct   21300
ggtgtgagaa cttctgagtt ggatgaaaca ttagccccag atcctagaag ccagggaagt   21360
gctggtcttt atcgactggc caccaggtgg cagatttggg caagggtctg cctttgggtt   21420
```

```
tagaattatt gcttaggcct taaagtagtt cttttttgcc agtgggagaa aatccctcaa    21480
agatggtttt ctgggttggt tggtttgttt gtctgtttgt ttgttttttg agacagagtc    21540
tccctctgtt attcagcctg gagtgcagtg gcatgatctc actgcaacct ctgcctctcg    21600
ggttcaagca gttctcctgc ctcaacctcc caagtagctg gaattatagg cacacgcccc    21660
cacacccagc taattttttgt attttttagta gagacagtgt ttcaccacgt tggccaggct    21720
ggttttgaac tcctgaactc aagtaatcct cccacctcag cctcccaaag tgctaggatt    21780
acaggtgtga gccaccgcgc ctggctcctc aaagatgtta atcctcttga tggcaattga    21840
ctaataccag aaaatgtcac gaagcgtgca ttttggattc aatcatggaa ttgttgagga    21900
caatcagcca tcagactaaa gcgatagaaa tagtattgga aattgcagcg ggagcactga    21960
atggagaagg cactccacat aatggaggag gcaaccaagt cttagagaag gtatcaagcc    22020
tgactataag gacagtgagg gaattgaaaa aacaaaaaag gagcaatgga gcagggaagg    22080
attgaatgcc tttcaagtag attcagtaat tgctgttagc agcaaaaaat gcagtagtgc    22140
ctgggcaggg ctttaaagtg cttgcacagg cagccctaga gggccgggct gcttgggaac    22200
tcttacaaac tgacctacca acttgagcat ccacagcctg atcagaggtg ggggagttaa    22260
gggccttctc tcccctagcc tctactagag cctgtaactg cagggaaacc aagttgcagg    22320
ctaaactctg cccacacatg cagacattga ttagcaagct acaaaaacag tcatgaaacc    22380
tgtttttata ggattagtga agccccagtt tgaccagagt actttgcatg aatgttttgt    22440
tagaagcaaa tgtgccaata ttctagcagc tgcgtttggt ttacttcttc ttcttctttt    22500
tttttttttt tgagttgaag cctagctctg tcacccaggc tggagtgcag ttgtgtgatc    22560
tcagctcact gcaacctctg cctcccaggt tcaagcgatt ctcccgcctc aacctcctga    22620
gtagctggga ttacagacat gtaccacaat acagggctaa gttttgtatt tttagtagaa    22680
atggggtttc accatgttgg ccaggctggt ctcaaactcc tgatctcaag tgatccaccc    22740
gcctcagcct cctaaagtgc tgggttaaca ggcatgagcc acggcacctg gcaaaagtca    22800
tcttttggtt tacttctatt gaactgaaaa agtcacaaat atatttatat ttaattaaat    22860
atatttatat aaaaatatgg tatttagtat tattattttt agagacaggg cctcgctctg    22920
tcacccaggc tggagtgcag tggcacaatc atagctcact gcagcctcaa gcttctgggc    22980
tcaagtgatc gttccacctc agcctcccta gtagctggga ctacaggcac atgccaccat    23040
actcggctaa ttatttttatt ttatttatgg gtctcgctat gtttcccagg ctggtctcaa    23100
actcctggcc tcaagcgatt ctctcacctc ggcctcccaa agcaccggga ttacaggtgt    23160
gtgccagcac acccagccac aaatctataa atttagaaag gaggactatt tctaaagagg    23220
gtcccactac ctgtaggcag gaagcagagc ctctggccat aactgaaaaa caagcacttc    23280
caagaagggg caaagggaac atgaatttat gctgagaggc gtagctaagc atacatattc    23340
aacagattat gggaggatct atgaatattc acaaagggag gatctatgaa tatgcacaca    23400
tgtggagtaa gctaacgtgt gcagcatgtc tcccatgttc accttaggca gaaacttaac    23460
actaacatgt attacagggc aacaaaatga gactgcatat ctacataacc tagctatttg    23520
gtaggctgaa gcaggagcat cacttaagac tgggagttcg aggcagctgt gagccatgat    23580
cgcaccactg ttctccagcc aggatgacag ggcaagaccc tgtcttagac cactctgtgg    23640
tcagtggtta tcaggaagga atgctagtca gttgtgctga aaccactaaa aaggaagggc    23700
agaattaggt gatgagttga taccagtggt gaagtgagtc ttttttttttt ttttcttttt    23760 gagatggagt cttgctctgt tgcccaggct ggagtgtagt ggtgtgatct cagctcatcg    23820
```

```
caacctccac ctcctgggtt caagtgattc tcttgcctca gcctcccgag tagctgggat   23880
tacaggcgcc tgccaccacg cctggctaat tttttatat ttttagtaga gactgggttt    23940
tgccatgttg tcaggctagt cttgaactcc tgacctcagg taatccaact gctttggcct   24000
cccaaagtgc tgggattaca ggcagctcca aagtgctggg attacaggca tgagccacca   24060
tgcatggcct gaaataattt ttttgaaagg gctagtttct atttagccct taggggaaaa   24120
aaaactaatg gcagttaggg agggaataga acgagtcctg tttgaactcc tttcccatca   24180
tggccaaaac ttaaaatttt ttttagatat ctctgggctc cccttggcca aaagatagtt   24240
tgttgagtca gttgggagct tagaattttg tttttatttc tcacatcatt gaatcaattt   24300
gaaccaggcg acaaaacctt ctgctcccag tagtgggtca gagaaccttc ctgattcctg   24360
ccctgagatt gtctctctga agacaacatt aggctagtag gctttccaga ttctgtaacc   24420
cattctttca aggaagagaa tgcctatatt tttctagcca attcatatac cttgagtatc   24480
actcaagggc aaaattattt ctaacaaatc atttactaat tagcaaatgc ttaagtgtag   24540
atttagaaag ctaaagctat acagtggctg ccatctatag tttggacttg tgattaacta   24600
cattgaaatg ctaactctgt accctagagt atgaattcct gattagagtc cttcaggtgc   24660
taactaattt atgtatttca tgtttgataa tattattact tgagctttgt gggagagcag   24720
tcttttcctc ccctgagata tagctagaag ttacctcctt tgtgaagcct tcctagatac   24780
tccaagcaga cacggtcctt cctttctccc ttgcccagca ctctgaggtt gactctgtgg   24840
agcactgatc cctctgtgtt ataattgtct atttacacgt cagctaccac ctataacaca   24900
ctgagttcct caacagcagg gacactgtcc attctttgat cccagtgtct ggaacagtgc   24960
caagtacata gtagggactt aataaatatt gattcatatg taaatgagac ttttccaaaa   25020
catgctttcg ttgatgcctc tcagcattta tacaccttt accaactcgc tactggccac    25080
atagacaaat gaaagcagta atccagatac acccaagagg acatctgttc ttttttctct   25140
ctgtggagtg ggagacttaa gtggcttctt aactggtgtg tcgtctgatc aagtggtcca   25200
ggtaacaggt ggatgccaat gtctggccca ggcatcaccc cttactggca ctggtcatta   25260
cagaagacac tctaccagag ctgaaaggac ctcttgtcac taggcagctg tggagtccgc   25320
tctacttgac ctagtaaaat ctgcctggag actgttagag tcaccccact acctgaagtt   25380
acctccaggc tgacctcttt ttttttcccag gtggagtcct ggcatcttag atattttaat   25440
aaggatttgc ttgttgacat gttctttatt cactaaggtg tcagcatatt actgtcttag   25500
aactgagggt tcttcatctt ttttggatca ggacctccct ctaagaatct gatgactgct   25560
ctggtccctc tcccaataaa aacttccata ctcacctgtt aaaaaaaaaa aaaactttaa   25620
acaaattaac agagttttat tcagcaaaga atgattcata atcgggaag gctgcaacca    25680 gaataggttc agagagactc cacggtgtgc cacgtggttg gagaggattt aggatttatg   25740
cacagaaaaa ggaaagtgac atgcagaaaa tgaaagtgag ggcctggtgc tggtgcggtg   25800
cctcacgcct gtaatcccag cactttggga ggccgaggcg ggcagatcat gaggtcagga   25860
gatcgagacc atcctggcta acacggtgaa accctgtctc tactaaaaat gcaaaaactt   25920
agccgggcgt ggtggcaggc acctgtagtc ccagctactt gggaggctga ggcaggagaa   25980
tggtgtgaac ctgggaggcg gagcttgcag tgagccagga tcccgccact gcactccagc   26040
ctgggcgaca gagcgagact tcatcttaaa aaaaagaaaa agaaaaagga aaatgaaagt   26100
gaggtacaga aacagccagg ttggttacag cttggtgttt gccttaaact tggtttgaac   26160
```

```
agttggccgc ctttgattag ccaaaactcg gtgattggta caagagtaga ttgcagttca   26220
ctatgtacag agaagccctt agatccgaac tcaaaatagg taaggaggca gttttagcta   26280
cacttaagtt aacatactca ggagtaccat tccagcttca agctggaagt gtctgcagcc   26340
ccctgagacc acttaatccc aagttaaaaa cccctgctca gaggcagcat cttttttttt   26400
tttttttttt ttttttttga gagagatctc actctgtcac ccaggctgga gtgcagtggc   26460
acgatctcag ctcactgcaa ccaccacctc ctgggctcaa gggattctct tgcctcagtc   26520
tcccgagtaa ctgggattac aggcgcgtgc cactatgtcc agctaatttt ttttttttgta   26580 tttttagtag agatggggtt tcaccatgtt ggcctggctg tcttgaaact cttgacctca   26640
agtgatccac tggcctcagc ctcccaaagt gctggcatta gaggtgtgag tcactgttcc   26700
tggcccagtg aggcaccatc tcattggata tggagacaaa ggatctggct tagcatcctg   26760
gatttgtatt ttcttccaa gagtccttaa gtgatatcta acttttgcga gctgcagttt    26820
cctcagctat gagatgagtg acattaacct cctctcttca gatttataag aggatcaatt   26880
aaaatggcat aggtaaaagt gcatcctagc aagttggtat ctactttaga aatgaaggag   26940
gtcatatgta tgtgaagtct ccagacccaa catgccatct tatatgtgtc tatttctaca   27000
agtgagctag tgacaacagt aattgctatt tttgctccta catgggtagg gctgatcttg   27060
actaggagga gtcaataaga ctcaccagcc gggcgtggtg gctcacgcct gtaatcccag   27120
cactttggga ggccaaggcg gcggatcac gaggtcagga gatcgagacc attctggcta   27180
acacggtgaa accccgtctc tactaaaaaa atacaaaaaa attagctggg cgtggtggtg   27240
ggcgcctgta gtcccagcta ctcgggaagc tgaggcagga aatggcgtg aacccgggag    27300 gcagagcttg cagtgaacca agatcgagcc actgcactct agcctgggtg acagagcgag   27360
actccatctc aaaaaaaaaa aaaagactca ccagctgtgg ccactgtctg tgctaattgg   27420
ctagtgcctg catctcagaa actgctacat attttgacta ttcccctgc acttaagggc    27480 atgcacactc ccaaaataga ctcagattgt ctaaggaata atgatgatga tgaagagaaa   27540
gccctcttta tctggtctat ttgtagtcag ttccaaaagc attaagaatt tctgctgaac   27600
taatgcagct agtttctttc ctgtcaccac tttccttcca aaatagtttc aagatctgtg   27660
ggggaaaaaa tctatttaca gtgaacagac tggtgggagg aagttgagca ttggggtttt   27720
ctgccctgtg taaccttgcc ctaagttggg cagatggtat cacactacct ggacatcatc   27780
tgctcattca ctatttgacc agttggtcat tcattcacaa atgtcctttt tgcaggaggg   27840
atggaggtgc tagacctgca gatgctagca tgaaaagaca gatctcctgc tgctaaggtg   27900
cttaaagtag tggaggtcag gggacaagca agcagtcagg cagctctgaa tgcagaggca   27960
ggaagcacca cgaggcaatg ggacccacag aggggtagca gggtagaggt gagtgggtct   28020
catgtgggga gggaggaagt tgactgcaga gaaggtgcca gggggtgaaa atagcttgag   28080
agctgtggag ctagaagggc tctcacattt gcttattaat atgcccttg aaaaagagtg    28140 gcctgatacc tggagtcact caaaagattt ccaattccga taggaaaaag tcaattttgg   28200
cttcagtggt tgcatgtgca cccctgatt tgctgtatgc tgaggcattg tggtgatgga    28260
cgcaagtgcg gagaccttga gcacgcatct gcccctagtt cttgccctga gtcctcgaag   28320
gaggcaggag agacatcaag gcagacaggc gccgctcatc agtgatgaga ccagacctgg   28380
aactcgcgtc ttatactcag tcctctgccc tttctgctgg attgtggccc ccagtatag    28440 ggtgcaacac acaactggag catttaaggg ccacaaagag aacaaattac caatgattgt   28500
gtgttgattc tttgagctct tttttttttat tattatactt taagtgttag ggtacatgtg   28560
```

```
cacaatgtgc aggttagtta catatgtata catgtgccat gctggtgtgc tgcacccatt    28620
aactcgtcat ttagcattag gtatagctcc taaagctatc cctccccct tccccctccc      28680 tccaccccac aacagtcccc agagtgtgat gttcccctc ctgtgaccat gtgttctcat      28740
tgttcagttc ccacctatga gtgagaatat gcagtgtttg atttttttgtt cttgcgatag    28800 tttactgaga atgatgattt ccagtttcat ccatgtccct acaaaggaca tgaactcatc    28860
attttttatt gctgcatagt attccatggt gtatatgtgc cacattttct taatccagtc   28920
tatcattgtt ggatgagctc tttatctcat ggaaaaataa tttataaaac tctgtatgag   28980
aggagtggga aatagtatta acgggtgcgg ggtttctttt tgggacaatg gaaatagctg    29040
gaattagata gtggtgatgt ttgcacactt tgtgaaatac taaaaactcc tgaattatac   29100
agttttaaga aactttttatt tatttgtttt tgagagaagt tctctgtgtc acccaggctg    29160
aagtgtggtg gcgtgatcac cggttattgc agcctcaatc tctgaggctc aagcgattct   29220
cccacctcag cctaccaagt agatgtgact ataggtgcgc accaccacac ccagtgaatt   29280
tgtaattttt tgtaaaaaca aggttttacc atgttgccca gtctggtctt gaactcctgg   29340
gcccaagcga tcctccctcc ttgggctccc gaagtgccag gatacaagca tgagtcacca   29400
catgcagcct cagttttaag aaacttttaa ataaatgaaa tatagtcata ccaaaacagt    29460
aaaaatgggt tcaggaaaaa aaatgttttt tttaaacaaa cttacgtatt gtataatccc    29520
agccctttta aaaaatgctt tcaaaaactg gcagtcaact cataaaagga caaatactta    29580
tgattccact gatgaagtag tcaaaagtag tcaaaaatca cagaaacacc accataaatg    29640
tataattttt atttttcaatt aaaaaaacat cttttttttta gtcaaaatca tagaaataga    29700
aagtagacag gtggttacta agggctatgg gatggggaaa ttagtgtcta atgggcatag    29760
agtttcagtg ttacaaggtg aaaagttcta gagttatgct gcccagcagt gtgaatatac   29820
tttattgttc tgtacactta acatggttaa tatggtaaat ttagcgttat gtgcttttta    29880
ctatagtaaa attaaaaaaa aaaaaatgg ggccgagtgc agtagctcac acctgtaaca    29940
taatcccagc actttgggag gccgaggtag gaggatcact tgaggccaga agtttgaaac    30000
cagcctggtc aatatagcga gacctcatct ctacaaaaga aaaatgttaa aattagacag    30060
gtgtggtgtc tgtagtccca gctctctgga ggcagggact gagtcagagg atcacttgag   30120 catagggggtt tgaggctgca gtgagccatg atcctgccac tgctgcagcc tgagcaacag   30180
agcaagaccc tgttgtaaaa acaaacaaac aaaaactggc agctgatacc tgagagtgaa    30240
tatcttttat cgctggttaa tgggattgag agaatgcttc atcttataga aagaacagtg    30300
tctttggacc cacagagacc tggatttaag attagctctg ccaattactg agtactcttt    30360
actatgaacc tctgttttcc tcatctgtga aactggaata atgaatccta ccgccaacaa    30420
ttgtagtcaa gttggaaaca atttacacaa agtgccaaac accaagcctg gcacagtagg    30480
aaccgagtaa atagtggtta atatttttat cagtgtctgc attgctgacg tctccatcat    30540
ttctatacat ttgttttttga atcagaaaaa gatgttattt taaaaaaata acccagtagt    30600 gcccctttgtc ccattcctat cagttatatt attattgtta ctaccctctg gaatttcaat    30660 aactcttttgt ttttttgggtt ttttgttttg ttttgctttg cttttgagac aggatctctg    30720
tcgcccagtc tggtgtgtag tggtgtgatc tcagctcact gcagcctcaa cctcctgggc   30780
tcaggtgatc ctcccacttc agcctcccaa gtagctggga ccacaggcgc atgccaccac    30840
acttggctaa ttttttgcatt tttagtagag acagggtttt gccatattgc ctaggccggt   30900
```

```
ctggaacttc tgggctcaag ccatctgcct gcctcggcct cccaaagtgc tggaatttca   30960
ggcatgagcc atgcctggcc taaatagctc tctgtgtttg caaaagtgtg ttataagaat   31020
cattcagagc ctctcgattg gatggaggct ctagaatgca cagaaaaagg ctgccaccgt   31080
gtatctctgc aagtcatgca caagatgggg aacagcaggc ttcccoctgc ttaccagttc   31140
aaatacagag aactagccct gtagctgttt ctttcatatc tcacccattc taaagagacc   31200
acaggcctta gaagtaaagg actcttttgt tgaaagagtg ttttcaaatt taaatgagca   31260
tttattggtc aaagatgcac caactagtct tttgaagaat tcaaggctct ttagagaaaa   31320
ataaagcctt ggaggagtat ctgagaagct tgttagatgc gtgggaagag tctggaaata   31380
aaaaacttca tctggagttt ctgccttcta ccaacagagc tgaagctaat gctctcctaa   31440
gacaagcaaa gcagtggtt tgcatacttc cttaccttcc ttttacttcc tctgtaatag   31500
acttgtcatg tctgatgttt gagttgacgt ggtactctaa tagagttaga gtctgcattt   31560
tttttatgtc ctctagtatg ttctggttga tggttgaggg caacaaacca gcagtcccag   31620
atgccagcac caagacctga gacaggtcac ttaactctcc gagcttcacc accattctca   31680
ccttgcagac ctcacaggga acagggaaag ctctatgaga tacaacatca ttatgattaa   31740
tcctattctg attctgaaag caaagctctt cctacacaaa ctcctatttc taaatactaa   31800
aagacatttc tttatggtgt attttgtgta cttgtagaaa tggaaagtgt tgagataaaa   31860
catgaagcaa tgatgacaaa gtgctaactt tttcttgttt taatttcttt atgctttttt   31920
tccacctaat cccctagagt ggtgtcttaa ctgtcaaact gggtggagat ctaggaacct   31980
atgtgatcaa caagcagacg ccaaacaagc aaatctggct atcttctcca tccaggtatg   32040
taggtatgtt cagaagtcaa catatgtaat tcttaaagac ttccgaaatg tgacattgtg   32100
gaccatttaa gaaatgtcgg ctgagcacag tggctgacac ctgtaatccc aacactttga   32160
gaggctgagg taggaggatc acttgaggac aggagttcag aaccatcctg gcaacatag   32220
tgagtccctg tctctgtaaa gaaaataaaa ataaagtcac agctgggtgc aggcttacac   32280
ctgtaatccc agcactttgg gaggccaagg cctgtggatc acttgagctc aggagtttga   32340
gaccagcctg ggcaatgtca caaagcccca cctctactaa aaatataaaa attagccagg   32400
tgtggtggca cacgcctata gtcccaacta cttggaaggc tgaggttgag cctcagcctg   32460
agcccaggag gtgaggttg cagtgagcca agatcgcgcc actgcactcc agcctgggca   32520
acagggccag accctgtccc aaaaaaaaaa aaaagtcat cgtcttatgt tagcatcctt   32580
gtaagtgagc ctttcctgat attttgcagc ctgtctcatt tcagtagaa aagtttactc   32640
tagttacata acttctccct gctgacaatt tggatactgt aagcaggcat caggatatta   32700
agatctgaag tgagtagctt ataacttttc caaatccagc ctagacagtt ttcctctatt   32760
aaattattgc cctgacttta aagaagcta cttttgacct tgtagcgttt gaacaagttg   32820
cactttgtct tcaaagcaag ttaaagtttg acctctactt gttttgagcc tctcaggtaa   32880
agggttattt gaattcccct tgcaggttgg ggttgtgtac cctgtggagg tggtagagtg   32940
ttatatattg ctgctccagg gcatttaatc cctcctgcct tttccattga tgtgctttca   33000
atctagagga ataaaagatt gtgttggaga cacaatgtgg cctgcatagc atctgaaagc   33060
ctgagaacat gcagggagag acatccctca tccctcagca gcctggctgc tgttgaagtg   33120
gttgtaagaa agtaaaagag aaatgccac aaaacgttct cagatccagt cattcattag   33180
cacttccaaa gagagcatgt tgactgtgaa ttggaaaggg gccagataaa actagcatag   33240
aattctttga aagactaacg gtatttgcat tttttaaaaa ttataacctt actctacccc   33300
```

```
ctaacattga catcattttt aggtaattaa tattttccca tttattattc tgtgatctct   33360
aatgctttgt tcagaataaa tagtgtgttt cctttcccca cactttcatc caagaagtgt   33420
gctagagttc aacaaaaaca gcactagaaa tcactgtcat tctaggaagg ccctaattca   33480
cagattgtat tggtttttag acccagttag tgtgctggag gttggaggat tttaacctct   33540
gtgggccaac tagcctctgt ggcctcagtc attcttcctg accctggctg tgcttgagcc   33600
tgtgtgttct tatccttcat ctccggggga acgaagtgga tcagctcggt ccagcgatca   33660
cttttgggga tcagtggctt tgtagatatc gggcaggcac ttaccccaaa agaactttcc   33720
ccatatctga agactgaaaa cgtccatatc gtatttggac acactgccca gcaatacgct   33780
ctagctgtgt tcagaagcat gggaatttgg aaagatctgc tgagcatgcc gtttactgtc   33840
acagatacta tcttcctcaa aaaaaaaaaa tatatatata tatatggggg acggggcagg   33900
ttgagactgg gtgagactga agaggtgcct tggccagagc aggccacacc cagagaccac   33960
aggctccccg gtccacctca ggcccctccc cttcctgcgc cgtttccggc agatccagag   34020
tggccaccgc cggatgggag tcgggggaag ggaggcagag aagcgggccc tgaggacaag   34080
ctctcagtgt ttctgtggga agtggcggca agacggcagc tcccagcggg ggatggaggc   34140
cgagtcagtc tgctggtcac tggaggccag gatgctgcct aacacagccg tcccgctccg   34200
ggcctcacca ccagggcggc tctccccact cccggcctgc tgcccacaca gactgcgggg   34260
ttccggggga gcaggaccca ggccgttctg cgcctgtctt cttggaagga gcaggccgga   34320
gcgcgggagc gccgtgtagc tgtacctgcg aaggcacagg attccgcggg aagatcccgc   34380
agtttcgggc cgtcgtcatt gtttttatac ctgtggcaaa tggcatgacc agacacacgg   34440
ttatgtctgg agaaacccct gtagaggagc aggaggttgt ggacatgctg tggcccggac   34500
agtggctgcc gagcagttgg agcctgcacc cgcccaactt ggctaaagaa gtccccatac   34560
tctctgtgga aaagatttcc agaagctgtt gtgtcaatat caaagcctca aaacaacaac   34620
aacaacaaca aaaacatgaa attatcaaca ataaagatca tccttgagtc tgctttgaaa   34680
agtagggtga aattctgcag aggcattcaa ctggcaagat accaccctca tagccagatc   34740
tgcaggtctc agccatcatg ccagggaaaa tgctccattc accactcctc agcttctgct   34800
tctggtttca gaggtctctg tattggaggg gctttaaagc aagaagggtc tttacccact   34860
tactcttatt cacagatgtg aatatgcagg tccagtgggg aaagtgacat gtcctaagtc   34920
agaatagagt caacaagaaa acagggccca aaatgactta gcctctagtg tataatgggc   34980
attgatgagc tactggaaat acagagatga agaaaacaca gtcccatctt caaggagctc   35040
aatctagcaa gggagacaga ctctttgtag gtgggaccgg gcttccctgc agcagaagga   35100
agcttgaaat tggtaacgag cctcagaagg gacagaggca ggccaccatg ctaccctgag   35160
aggatcgcat gtggacacgg ggctatgacc tggccctgct ttgacccact agctgtgctg   35220
tagggccagg tggagcctgg agtggcctgt gctaagggc tactatgagc tctttccact   35280
cccccaaggc attgcataaa taatgtcact ttctgtttgc acagcaaaat cagggacaca   35340
atttctaga acatggggtg cctcccctcc ccccagccca acagaagttc tacaatgact   35400
gatgggccct tgttttgtt tgagacgaa caccccacag ggttccgagt ggtgatttgt   35460
ggcccacagg ccactggcaa gtggaggcag agctgcagag ccctcgggag ccacagaggg   35520
cctgctggcc gccacgacat gccaactcag ctgctgctgg ccctcctgtg gcggcagtg   35580
ctagtgatgt gcagaatctt aggactagtg ccaaggaacc tataaatacc ctgggtgacc   35640
```

```
caggcgtgca ctgctgtggt ggccttcaca gtcagaagat gacaagctga aaggggaga     35700 atcggcccaa ggtgagatcc acagaaaggc cagggccaag atgcggccag cacctcaggc     35760
tggtggtggt cttacgttga ccatgccaga ggccagtcct tgattgctcc aaaccctctg     35820
ttcgagggtt ccaaatgaaa tgagcaggtc ctcgtgtcag gacctaggtt agtttctgaa     35880
aaagcatgaa aagcaggcct cctgaacttc cccgagtgac tgatgcaaag tgcgtcctgc     35940
atgcttcaca gcaccatgga gaggatcttc aggggcaaac tgcagactat ctgaatgacg     36000
gcactgacca tcagcaaacc gcagagctgc ctgaccaaga aattgcgaga cagaagcaat     36060
gcttgcaggc gaagaagaag gggccagaca cagtggctca cgcctgtaat cccagcactt     36120
tgggaggcca aggcaggcgg atcacttgag gtcaggagtt tgagaccagc ctgggcaaca     36180
tagtgaaacc ctgtctctac taaaaataca aaaattcgc caggcatggt ggcaggcacc     36240
tgtaatccca gctgcttggg agactgagac aggagaattg cttgaaccca ggaggcgaag     36300
gttgtaacga actgaaatcg tgccacagca ctccatcctg ggcgacagag tgagactgtc     36360
tcaaaaaaag gaggagaaga aggaaaggcc aaggcaggaa tgaaacaggc catgaatgtt     36420
ggagtgaagc aactggcctc ctcgtgctaa gcggctactg tgagttcttt ccactccccc     36480 aagcattgc ataaataatg tcactttctg acactcaccc cgctgaatgt cctgcctctg     36540
ctcaagggtg gtatgatggg gacttggcag tggaggggaa cagggaaacc agacatggtg     36600
gtctccccgc ttcctggcta caagtccctc tgaagaaatc caaaggagta aagagcttgg     36660
agagtaggcc tctgtagggt gcaagggcac agctggagac ggagctcctg aggctgcagc     36720
tgatgctgcc cgctctgcct gaactgcacc aaaaacgtga tgaggccata gcgggagtcc     36780
acggaggagg atgcctactg cccgacctct agcagagact aagcaaggtg catgaaaact     36840
tgaaccacat gtgtcacacc catgaccact acatgaagat ggcccaaaac ctggcccagg     36900
aattgaagaa agactcttcc aatttgctgt aagaaatgg cccaggggc aagcacggta     36960 gctcacacct gtaatcctag cactttggga agctgacgca ggcagatggc ttgagctcag     37020
gagttccaga ccagcctggg caacatggtg aaaccccgtc tctaccaaaa atacaaaaat     37080
tagccgggtg tggtgatgca tgcctgtggt cccagctact caggaggctg aggtggaagg     37140
attgcctgag tctgtggggc agaggttgca gtgagctgag atcacaccac tgcactccag     37200
cctgggtgac acagtgagac cccatctcaa aaaaaaaaa aagaaagaaa acggcccagg     37260
aaggctggag ggccgccgtg tccattgaga gagtgctcca ggcactccaa aaagaaaatg     37320
accacaatgg gaagaaacca gctgaccatg agaccaagtt ccaaccttt acaagtggcc     37380 tgtggctcct ggcgccccgc ccacagctga caggggctca gaagtgctag ggggaccatg     37440
ggccaccagg gccaccagga gggaggcagg taacgatgcg agggcttgga tgcagaacac     37500
cagctggttt gattctgttt tccctgtacc tgggtcctga atgcccagag gctcagggaa     37560
acaccagcca gtgctgctgc cttaaagca cttttgactg atctcttgtt aatttagcaa     37620
ctgttattgg ttgatgctgc agttgctctt attgaagttt gattgatagc attaggatgg     37680
taaggcacta ttttcaaat aaaggttgtt taatataaaa aaaattttgt ttttttct     37740 ctcagccttt cacattggtt caaaatatct ttcatctggc tgcatttctg attttttgttt     37800 tgttttttt ttcttaattt tatttatttt taattaaaaa taattttttt tgtcaacatg     37860
gggtctcact tgttgccta ggttggtctg aaactcgtgg cttcaagcaa tcctcccaca     37920
tcagcctccc aaagtgctgg ggttatgggt gtgagccact gcagcagcct gttttttttg     37980
tttgtttgtt ttttttaatt tgacaagttt tcaggtcctg tgaaatcagc agtcttacct     38040
```

```
cccaccttgc gcaccctgag gaggttgcag aataaaggag aattctaggg acacgtgggc    38100
atcagtgcct gtgctcagag cacctcaggc agtgtggagg ggtctagagg ttactcaggc    38160
tctgcctggc aacccgatag cagtatcaga gtatagggcc aaggggacgg tccttgggct    38220
tggtgtggtt tattagtcct tttcctgtga ccctgatggt ttggttcact catttttatc    38280
tccatactgg gaacaggttc aagccccagc atttggttga taatgcagga atccttgata    38340
cttttattgc ccaagcttcc cttcctggtg acctcatcct agcctcagtc tttgaaaaag    38400
ccctccttga gtgctcaggc agactcaggt gcccttcctt ctgggctccc atgcactctg    38460
ttcttacctc catcagggtg ccacatgcac tagtgttatc tgctgccgtg gccaatcatc    38520
catgaggcca tgaggaagtg gaatgtacat ctggtataag aagacatggc agaagccagc    38580
ctccgatctg tccacacgaa tacagcattc ccaaagcaac gtgcatgtgc cattattcac    38640
tggatgagct tgaggtggat gaactagccc accaggctct caatgtcatg aatttaacac    38700
tgaattaaga aaaatatgtt ttaaaaataa tagtttaggt gattgctggg gtgctaggag    38760
aggaaggaat ggggaataac tgtttaatgg gtatagttgg ccttgtgtat ctgtgggttc    38820
cacatctgat tcaaccaacc gtggatcaaa atatttgaaa ataaaaaaca aaacaaaaat    38880
gatacaaata aaaccaata taacaactat taacagcatt tacattgtac taggcattat    38940
aagtaatctg gagatgactt aaagcataca gaaggatgtg cctaggttag atgcatgtat    39000
cgtaccattt catatcaggg acttgagtac ccacggattt tggtatctgc agatcctgga    39060
accccttccc tatggatacc aaggaacaac agcactgggt ctccttttgg ggtgatgcag    39120
atgttttgaa gctaggcaga ggtagtggtt gcaacacatt gtaaatgtac taaatgccac    39180
caaattattc attttttaaat ggttaatgtg ttatgtgaat ttcaccttaa caactaataa    39240
tattataggt aaggcacaag ttacatctgt agcacaaaaa tggccctaat ttttaaaaca    39300
ctgctccagc atagcaggta tcacatgtga ggtagcaaaa gctggagatc aaagtgtgat    39360
acctggagac ttatcagtaa gggtcaaatg ttttttcagg ttttgagaat cattcttgga    39420
attgttccag aagatatatc gtataactct tcttagatgc taagataaga aggcagatat    39480
acactagctc attttgtgtt attttctaga gctttactcc agtcaatttc ttgggggcag    39540
catttgtgga atcagtggtt catctgaagg gctgtgctgt ggaattacta tgcatttgtt    39600
ttgtcttcca gtgacctaa gcgttatgac tggactggga aaaactgggt gtactcccac    39660
gacggcgtgt ccctccatga gctgctggcc gcagagctca ctaaagcctt aaaaaccaaa    39720
ctggacttgt cttccttggc ctattccgga aaagatgctt gatgcccagc ccgttttaa    39780 ggacattaaa agctatcagg ccaagacccc agcttcatta tgcagctgag gtctgttttt    39840
tgttgttgtt gttgtttatt ttttttattc ctgcttttga ggacagttgg gctatgtgtc    39900
acagctctgt agaaagaatg tgttgcctcc taccttgccc ccaagttctg attttttaatt    39960 tctatggaag attttttgga ttgtcggatt tcctccctca catgataccc cttatctttt    40020
ataatgtctt atgcctatac ctgaatataa caaccttaa aaaagcaaaa taataagaag    40080
gaaaaattcc aggagggaaa atgaattgtc ttcactcttc attctttgaa ggatttactg    40140
caagaagtac atgaagagca gctggtcaac ctgctcactg ttctatctcc aaatgagaca    40200
cattaaaggg tagcctacaa atgttttcag gcttctttca aagtgtaagc acttctgagc    40260 tcttttagcat tgaagtgtcg aaagcaactc acacgggaag atcatttctt atttgtgctc    40320
tgtgactgcc aaggtgtggc ctgcactggg ttgtccaggg agacctagtg ctgtttctcc    40380
```

```
cacatattca catacgtgtc tgtgtgtata tatatttttt caatttaaag gttagtatgg    40440
aatcagctgc tacaagaatg caaaaaatct tccaaagaca agaaaagagg aaaaaaagcc    40500
gttttcatga gctgagtgat gtagcgtaac aaacaaaatc atggagctga ggaggtgcct    40560
tgtaaacatg aaggggcaga taaggaagg agatactcat gttgataaag agagccctgg     40620
tcctagacat agttcagcca caaagtagtt gtccctttgt ggacaagttt cccaaattcc    40680
ctggacctct gcttccccat ctgttaaatg agagaataga gtatggttga ttcccagcat    40740
tcagtggtcc tgtcaagcaa cctaacaggc tagttctaat tccctattgg gtagatgagg    40800
ggatgacaaa gaacagtttt taagctatat aggaaacatt gttattggtg ttgccctatc    40860
gtgatttcag ttgaattcat gtgaaaataa tagccatcct tggcctggcg cggtggctca    40920
cacctgtaat cccagcactt ttggaggcca aggtgggtgg atcacctgag gtcaggagtt    40980
caagaccagc ctggccaaca tgatgaaacc ccgtctctac taaaaataca aaaaattagc    41040
cgggcatgat ggcaggtgcc tgtaatccca gctacttggg aggctgaagc ggaagaatcg    41100
cttgaaccca gaggtggagg ttgcagtgag ccgagatcgt gccattgcac tgtaacctgg    41160
gtgactgagc aaaactctgt ctcaaaataa taataacaat ataataataa taatagccat    41220
cctttattgt acccttactg ggttaatcgt attataccac attacctcat tttaattttt    41280
actgacctgc actttataca aagcaacaag cctccaggac attaaaattc atgcaaagtt    41340
atgctcatgt tatattattt tcttacttaa agaaggattt attagtggct gggcatggtg    41400
gcgtgcacct gtaatcccag gtactcagga ggctgagacg ggagaattgc ttgaccccag    41460
gcggaggagg ttacagtgag tcgagatcgt acctgagcga cagagcgaga ctccgtctca    41520
aaaaaaaaaa aaaggagggt ttattaatga gaagtttgta ttaatatgta gcaaaggctt    41580
ttccaatggg tgaataaaaa cacattccat taagtcaagc tgggagcagt ggcatatacc    41640
tatagtccca gctgcacagg aggctgagac aggaggattg cttgaagcca ggaattggag    41700
atcagcctgg gcaacacagc aagatcctat ctcttaaaaa aagaaaaaaa aacctattaa    41760
taataaaaca gtataaacaa aagctaaata ggtaaaatat ttttctgaa ataaaattat     41820 ttttgagtc tgatggaaat gtttaagtgc agtaggccag tgccagtgag aaaataaata    41880
acatcataca tgtttgtatg tgtttgcatc ttgcttctac tgaaagtttc agtgcacccc    41940
acttacttag aactcggtga catgatgtac tcctttatct gggacacagc acaaagagg    42000 tatgcagtgg ggctgctctg acatgaaagt ggaagttaag gaatctgggc tcttatgggg    42060
tccttgtggg ccagcccttc aggcctattt tactttcatt ttacatatag ctctaattgg    42120
tttgattatc tcgttcccaa ggcagtggga gatccccatt aaggaaaga aaggggcct     42180 ggcacagtgg ctcatgcctg taatcccagc actttgggag gctgaggcaa gtgtatcacc    42240
tgaggtcagg agttcaagac cagcctggcc aacatggcaa aatcccgtct ctactaaaaa    42300
tattaaaaaa ttggctgggc gtggtggttc gtgcctataa tttcagctac tcaggaggct    42360
gaggcaggag aatcgctgta acctgggggg tggaggttgc agtgagacga gatcatgcca    42420
cttcactcca gcctggccaa cagagccata ctccgtctca aataaataaa taaataaata    42480
aagggacttc aaacacatga acagcagcca ggggaagaat caaaatcata ttctgtcaag    42540
caaactggaa aagtaccact gtgtgtacca atagcctccc caccacagac cctgggagca    42600
tcgcctcatt tatggtgtgg tccagtcatc catgtgaagg atgagtttcc aggaaaaggt    42660
tattaaatat tcactgtaac atactggagg aggtgaggaa ttgcataata caatcttaga    42720
aaactttttt ttcccctttc tatttttga gacaggatct cactttggca ctcaggctgg    42780
```

```
aggacagtgg tacaatcaaa gctcatggca gcctcgacct ccctgggctt gggcaatcct    42840
cccacaggtg tgcacctcca tagctggcta atttgtgtat ttttttgtaga gatggggttt   42900 caccatgttg cccaggctgg tctctaacac ttaggctcaa gtgatccacc tgcctcgtcc    42960
tcccaagatg ctgggattac aggtgtgtgc cacaggtgtt catcagaaag cttttttctat  43020 tattttttacc ttcttgagtg ggtagaacct cagccacata gaaaataaaa tgttctggca   43080
tgacttattt agctctctgg aattacaaag aaggaatgag gtgtgtaaaa gagaacctgg    43140 gttttttgaat cacaaattta gaatttaatc gaaactctgc ctcttacttg tttgtagaca   43200
ctgacagtgg cctcatgttt tttttttttt taatctataa aatggagata tctaacatgt   43260
tgagcctggg cccacaggca aagcacaatc ctgatgtgag aagtactcag ttcatgacaa   43320
ctgttgttct cacatgcata gcataatttc atattcacat tggaggactt ctcccaaaat   43380
atggatgacg ttccctactc aaccttgaac ttaatcaaaa tactcagttt acttaacttc   43440
gtattagatt ctgattccct ggaaccattt atcgtgtgcc ttaccatgct tatattttac   43500
ttgatctttt gcataccttc taaaactatt ttagccaatt taaaatttga cagtttgcat   43560
taaattatag gttacaata tgcttttatcc agctatacct gccccaaatt ctgacagatg   43620
cttttgccac ctctaaagga agacccatgt tcatagtgat ggagtttgtg tggactaacc   43680
atgcaaggtt gccaaggaaa aatcgcttta cgcttccaag gtacacacta agatgaaagt   43740
aattttagtc cgtgtccagt tggattcttg gcacatagtt atcttctgct agaacaaact   43800
aaaacagcta catgccagca agggagaaag gggaaggagg ggcaaagttt tgaaatttca   43860
tgtaaattta tgctgttcaa aacgacgagt tcatgacttt gtgtatagag taagaaatgc   43920 cttttcttttt ttgagacaga gtcttgctct gtcacccagg ctggagtgca gtggcacgat  43980
ctgggctcac tacaacctcc gcctcctggg ttcaagcaat tctctgcctc agcctcccga   44040
gtagctggga ttacaggtgc ctgccaccac acccggctaa ttttttgtatt tttagtagag  44100 acggggtttc accatcatgg ccaggctggt cttgaactcc tgacctagta atccacctgc   44160
ctccgcctcc caaagtgctg ggattacagg cgtgagccac tgcacccagc cagaaatgcc   44220
ttctaatctt tggtttatct taattagcca ggacacttgg agtgcatccc gaagtacctg   44280
atcagtggcc cctttggaat gtgtaaaact cagctcactt atatccctgc atccgctaca   44340
gagacagaat ccaagctcat atgttccatc ttctctggct gtatagttta aggaatggaa   44400
ggcaccagaa cagatttatt gaaatgttta ttagctgaag atttatttag acagttgagg   44460
aaaacatcag cacccagcag taaaattggc tctcaaagat tttcttctcc tgtggaaagt   44520
cagacctctg aggccccatc caggtagaag tactagtgca agaagggcct ctgctgtcca   44580
cttgtgtttc tgtgatctgt gggaacattg ttaacgccac atcttgacct caaattgttt   44640
agctcctggc cagacacggg ggctcacacc tgtaatccca gcactttgag aggctgaggc   44700
aggtggatca cctgaggtta ggagttcgag gccagcctgg tcaacatggt aaaaccccgc   44760
ctctactaaa aatacaaaaa ttagctggcc gtagtggcgc acgcctgtta tcccagctac   44820
tcgggaggct gaggcaggag aattgcttga acctgggtgg tggaggttgc agtgagccga   44880
gattacacca ctgcactcca gcctgggtga caagagggaa actccattaa aaaaatgtaa   44940
ttcccgtgtc tgccatctta agtgtaaagg tggctaaatt atatagaaaa ataagacaat   45000
atcatttccc aattacattc ctttcctacc gcactctatg atgctagctg agattttttcc  45060 aaagaaaat ggcttaaata aaaccctaag agaaagaaaa actttaaatc cctccaaagc    45120
```

```
tcaaaagtaa tagaaacaga tgagtttgga gtcaggattt ctctgtaaga ttgcctaggc    45180
tgtgtactgc acatctccag gtgccactgt tgacagagat tataactaca atgtgaagtg    45240
aatggtgcca ctgacagtta tgcaaaccgt ccagagcata gccacctgat cctgctggga    45300
ttcctcttgc cagtccatca gcagttcccc ttgaaagttt caccaaacat cccttaaatc    45360
tgccctctcc tgcccgtccc cagtggaggt cctcatcatt tttcacctgc attttgcag     45420 gagctttctt atatccacct tcctcctttt ctctcagccc atcatctagc tacacagtct    45480
ccagggtaag ctttcagaaa ggcaatctct tgtctgtaaa acctaagcag gaccaaggcc    45540
aagtttctta gcctgaaaaa tgtgcttttc tgactgaact gttcaggcac tgactctaca    45600
tataattatg cttttctacc ccctcacact caacactttg actccagcaa tcccaaatcc    45660
ccagatccct aagtgtgctg tgctattttc acgtggctct cagacttggc cagtgctgtt    45720
tccattttgg tctttattcc ccacatctct gcctgggggg tagattctac cctgaaaaat    45780
gttcttggca cagccttgca aactcctcct ccactcagcc tctgcctgga tgcccttgat    45840
tgttccatgt cctcagcata ccatgtttgt cttttcccagc actgacctac catgtgtcac    45900
ccctgcttgg ctgtaccttc catgaggcta ggactatgtg tctcctttgt tgactgctgt    45960
tgccctagca tcttgcacag ttccttgcac acaattagag ctctataaat gtcaaataaa    46020
tgtgttataa ttatatgttt aagatagttg ttcaaataaa ctctaaataa ccccaactcc    46080
aagagtgtta gcaagaaata taaatttttac agaagaatgg ttggaggtgg ggagggtgtc    46140
cacggagtga gttacctcac acaggcacgg aaaaacttga acctcctaag gacattttta    46200
agctctcttt cccatttttct ctcctggatt cccattgcct ggtctcattt ctctcttctc    46260
caccacacca cttcctcaaa aattcccttta gggtttgttc ttaagcttag ataggtttcc    46320
cattctgaaa tacaaaggcc tgataattag ccaacttacc ttgttgggga tgtggaaggc    46380
aagactctca gactccatga ctcaggtata ttgcaacaat taggctgaaa gttccttgag    46440
agtaagtgtc caaatctttt catgtttggt tcccagggct cactacagtt gttggtatat    46500
cataggcact ctaatatctt cttaaagaat caatatcatt aaaatggcca taactgccca    46560
tagcaattta cagattcaat gctatttcta tcaaactatc aaggtcattt ttgttttatt    46620
tttttctttt gagatagaat ctcgctattg tcacccaggc tggagtgcag tggcgcgatc    46680
tcgactcact gcaacctccg cctcccgggt tcaagtaatt ctcctgcctc agcctcccga    46740
gtagctggga ttacacgtgc ctgccaccac acctggctaa ttttttgtatt tttagtagag    46800 acaaggcttc aacatgttgg ccaggctggt cttgaactcc tgacctcagg tgatccacct    46860
gccttggcct cccaaagtgc agggattaca gcatgagcca ctgtgcccgg cccatggtaa    46920
tttttcacag aatcagaaga aactattcta aaattcatat agcggccagg cgaggtggct    46980
cacgcctgta atcccagcac tttgggagac agaggcagga ggatcatctg aggtcaggag    47040
ttcgagacca gcctgtccaa catggtgaaa ccctgtctct actaaaaata caaaaatttg    47100
ccagtcgtga tggcgggcac ctgtagtccc agctactcga gaggctgagg caggagaatt    47160
gcttgaaccc gggaggtgga ggttgcagtg agccgagatc acgccactgc actccagcct    47220
gggcaacaga gtgagactcc atctcaaaaa aataaataaa ataaaataaa ataaaattca    47280
tatagaacca aaaaagagcc caaatagcca aagtaatcct gagcaaaaag aacaaagctg    47340
gaagcatcac attacccaac ttcaaactct actacaaggc tatagcaact aaaacagcat    47400
ggcactgcta caaaaacaga caggtagact aacggaacag aatagacaac tcagaaataa    47460
agccacacac ctacagccat ctgaacttgg acaaactcaa caatattaag taatggggaa    47520
```

```
aggactccct attcaaaaag tagtgctggg ataactggct atccatatac agaagaatga   47580
aactagactg ctacctatcc ccatatacaa aaattaaatc aagatggatt aaagacttaa   47640
atgtaagatc tcaaactaaa aaatcctaga agagccaggc gcggtggctc atgcctgtaa   47700
tcccagcact ctgggaggct gaggcggatg gatcacctga ggataggagt tcgaggccag   47760
gctggccaac atggtgaaac cctgtctcta ctaaaaatac aaaaattagc tgggcatggt   47820
agtgtgtgcc tgtaatctca gctactcggg aggctgagac aggagaatcg cttgagcctg   47880
ggaggcagag tgagcccaga tcgcaccatt acactccagc ctgggtgaca ggagcaagat   47940
tccatctcaa aaaagaaaa agaaaaaaaa aatcctagaa gaaaacctag taaatgccct   48000
tcttatatca gccttgacaa agaagttatg actaaatcct agaaagcaat tgcaacaaaa   48060
acaaaaattt acaagtggga tctaattaaa ctaaagagat tctgcacagc aagagaagct   48120
atcaagggag taaacagaca gcctacagaa tgggagaaaa tattcacaaa ttatgcatct   48180
gacaaaggtc taatatccag aatctataag gaacttaaat caacaagcaa aaaccaaata   48240
accccattaa aaagtaggca aaggacacga acagacatgt ctcaaaagaa gaaatacaag   48300
tgaccaacga acatgaaaaa atcctcatca tcactaatca tgagagaaat gcaaatcaaa   48360
agcacagtga gatatcattt cataccagca agaatgacta ttaaaaaagt caaaaaataa   48420
cagatgttgc aagactgcag agaaaagaga acgtttatac actgttggta ggaatgtaaa   48480
tacattcaac cactgtggag aacagtttgg agatttctca aagaactgaa ttgaactacc   48540
agtcgaccca gcaatgccat tattgagtat atgcccaaag gaaaataaat tgttctatca   48600 aaagacaaa tacacccatg tgttcatcac agcactattc acaatggcaa agacatgaaa   48660
ccaaaccagg tgctcatcaa tggtggatta gattgtgtac atatatacca ccatatggta   48720
catatacact gtggaatact atgctgccat aaaaaagaat gtaatcatgt attttgcagc   48780
aatatggatg tagctagagg ccattattct aaacaaacta acacagaaac agaaccaaa   48840 taatgcatgt tctgacttaa aagtgggagc taaacactga atacacatgg gcataaagat   48900
gggaacaata gacagtgggg gctattagag aggcaagggc tgaaaaacta cctattcggt   48960
gccctgctca ctatctgggt gacagagtca ttagcactcc aaagctcagc atcacacagt   49020 ataccttgt aacaaacctg cacatgtacc ccctgattct aaaataaaag tcgaaggaaa   49080
acaacaaaaa caaaagaaa taactcctga gttgggtct ccatctctta gttcagccta   49140
ttggcagtcc ccttttcaa gttctaagga gcctgtacta gactactctt catttagtcc   49200
cataataatc cctctttcaa ttattttgcc ttcaaaccta tagggaaggg attggaaatg   49260
aagtttcagt cattccctaa gtaaaatgta tatacatatt ttaattgaaa caggatttca   49320
ctctgttgcc caggctggag tgcagtggtg tggtcatggc tcactgcagc ctcaacctcc   49380
tgggctcaag caatgcttcc atctcatcct cccaagtagc tgggactaca ggctcgtaaa   49440 tttttttagag aacaaaaaca cagtctttag atttaaacat gtgaaagcag aaatttttaaa   49500 aatacaatga aagagttgga agacagagtt gaaattgttc agaaattaca gtaaaaatac   49560
taagagatag gaaatagtca acttccaaat gagaagaatc acgaaagaga gaacagaaaa   49620
gatagaaaaa aaattatcaa agaaataatt caagaacatt tccttaaagt gaagggcatg   49680
agattccagg tatattccac atatagaaaa atatcccata caaatcaca ttgttatgaa   49740 ttttcataac atgagggaca aaaaagata atataagtaa ccagagaggg aaaaaataaa   49800
taaacaaaac aagacaaata ggtcatatac aaagtaatat tcatcacaat agcttcatag   49860
```

```
ttctcaataa taacaaaaag cctttaaaat tctggttgaa gcagttcaga caatgccatc    49920
acccaaaaat atgccatttt ggcatactga ttattattag ctgaaagcac ttgagaaaca    49980
gcagactgta caggaagggc tttccaacct cctcttttct acctaaaaac aggctagaaa    50040
atttcccatg ataaaggtgc cctccctcta ctagaaagag aaaaacatcc ttatcaccag    50100
agatagggaa tcaatgccaa aatggatctg aacaaactta ttggaataac ccttgtcttc    50160
cactacttat ccccaatata gctcttagta atttccccaa gcccctttgt cttgtcattt    50220
cttcacaaat ttatcatttc tttgtctaaa acatatataa acttgtctgc tatggtgact    50280
tcttcgggtc tacatttgct tgtgaggact cccaggtaca tgtaaaattg taataagact    50340
tgcgtgcttt tctactgtta atcttcctg tgtcagttta attcttaggc ctagctggaa     50400
acttaagagg gtagaacaga aattttcct ttcctacatg gtgaagggac attctgtaat     50460
aaaactagcc tcaacattaa aaaatgtga tgtaataaaa aacaaaggaa aaagaaaaca     50520
aaacagaaaa gcaattaata acactaggaa acacgaggca ttgtacagga taggaaacgt    50580
cctgttatgt tacacaatgc aacagtgggt attgttttca tcattattat aatgaaaatg    50640
ctaaatagtg atttgaccaa caatccagtt taaaacattt ggaggaatgt gaatgtttat    50700
ggccagaaaa tggggagaaa aatggttaag gaaacaaaat ctcatcatct agagtgggaa    50760
ggagactgat aattcctaat atgaaccaaa aactcaaact tttttttttt tttttgagat    50820
ggggtctcgc tctgtcgccc aggctggagt acagtggcac gatctcagct cactgcaacc    50880
tctgcctccc aggttcaaga gattctcctg cctcagcctc ttcagtattt gggactacag    50940
ttgcacacta tgatgtctgg ctaattttg tattttagt agagatgggg tttcgccatg      51000
ttggccaggc tggtctcgaa ctcctgacct cagatgatca gtccgccttg gcccccaaa     51060
gtgctgggat tacagacatg agccattgca cctggcctga aaactcattt tatttagata    51120
tgttaaggga aatctcaaaa taatcagcta gaaaaattga aatggttgc ccatgaggag     51180
gggagaactg ttattattta tgtcaaataa aatttgtagg aagccattga tttggactgt    51240
gctcctgcac taggccccaa tagaccaaac cacatggagt cactcttgct aaagttccac    51300
gtcaccaaac caaagctaag tagtttatct taccttctgg gaaattaggg gagagaaata    51360
atagacaaat ccccaaacag gccagtttta gctggcatat aaggaagtcc tctctgtttt    51420
aaccgtatta ggagagtaac tttgaaaaga ccgtccactt tttggtccct gtttctgttt    51480
tcttctgcct tttctgccta taaagctaac ttcctctgcc cagctcactg gagtaccttc    51540
tctgaatttt tagaagacag gctgccctga tccatgaatt gcaaatgaaa gccaattaga    51600
tcatttaact aaattcattg taattttgtc ttttgacatt tgtaaacaag ccttgtagta    51660
cttgctaaac aatgggctgg gcgcagtagc tcacacctgt aatcctagca ctttgggagg    51720
ctgaggtggg tggatcacct gaggtcagga gttcgagacc agcctggtca acatggtgaa    51780
actccgtctc tactaaaaat tcaaaagtta gatgggcatg gtagcatgtg cctgtagtcc    51840
cagctactca ggaagctgag gcaggagaat tgcttgaatc tgggaggcag aggttgcagt    51900
gagctgagat agtgccactg tactccagcc tgggcagcag agcaacactc tgtctcaaaa    51960
aaaaaaacaa aaacaaaaac aaaaaaacaa cttgctaaac aacatatgtt tattatttgg    52020
taaattataa acaataaatt caaaacttta aaaagaaaac attttattga tagctcactg    52080
aatacaaatt tataaaatat tatttatgca ttaagtttca gttacacatt ttcacccatc    52140
attacagatg tcatatggag ttgctagagt atgagaagag cttcttcatc ccaacagctt    52200
tcaaagtgaa gaggcgactc atgcctgtaa tcccagcact ttgggaggct gaggcgggtg    52260
```

```
gttcacttga ggtcaggagt ttgagaccag cctggccaac atggtgaaac ctcgtctcta    52320
ctaaaaatac aaaaattagc tgggcgtggt ggcgcacacc tgtaatccca gctactcagg    52380
aggctgaggc aggagaatca cttgagcccg tgaggtggag gttgaagtga gccaagatca    52440
tgccactgca ctccagcctg ggtaacaaag caagattctg tctcaaaaaa aaaaaaaaaa    52500
aaaaagtgaa catctgggtc ccccagatct cttcagagat atgtaatgtt ctccttttc     52560 caactacata actctttaag ctgggttttc ttcatatact ccaatgaaaa caacatattg    52620
caacagatgg aatgaagagg caagtagaag aatccagctg ttttctatta agccaaacat    52680
tacaattgtc agctgaagaa ttctgagatt cataaatttg gaaagaaaag cttcatttct    52740
cataaaagat tgcagcctgc agggtggcca ttctgacagg ctaagaaatg tagtctctgg    52800
ccagaagcca aaaacagaca ctgagggtca gaagaataag atgggcattt atgctgaata    52860
ggatggccaa atatacatat tcaataaact acagtcatga atattcatga aggagaaac     52920 atgcacatgc tcaattgagc ttcatgcctc tccatgggac gcgtgtgcaa aaaatggcag    52980
cattagcatg atcagagggt ggagttttct gtcctctgat atcaaaaggt gaaacagagg    53040
acacagaaac cctcactgca catcctctgt aaactggcca gaaccactcc attgtgggca    53100
gtctgttatc aggaaggaat gctggttagt tgtgcagaaa ctgcaaaagg aagggcagt     53160 gtcagaccat tggttgatat cagcggtgca gctcgtcttt ccaaagggct ggtttctgtt    53220
taacctgtag gaaggaaatc ctaatggcgt ttagcaatgg agagggtata acaacacatc    53280
atggcaagaa ctcagttttc aaggtttctc tggggtcccc ttggccaaga ggtggtgcat    53340
ccgtttagtc agctggggga cttaggattt cattttatt tctcagagtt ttataaaact     53400 ctaaataat tatttgacag ccaggtggga ggggtccct ggagaaactc caaccagcct      53460
gcctactagg gtggagcctt gggagtttgc agcagggagg agcctggcgc tcctcttcc     53520 tatgtgaacc tgggattcta gcagcctggt gggaagcact gtagcaggag actctggcct    53580
tgcagaggat ccctgttccc ctcatccctt tatttcccct tttcacttaa taaaaccctg    53640
ctttactcac cctttaaacc atctgcaagc ctaaattttt gtggctgtgg gatagacaag    53700
aaccttctct ttagctgaac taaggaaaag tcctgcaatg atcccattct tcacaccaaa    53760
tatgttttgt ttcaaaagta tagttattta tcataaatat gtcattaata ttgttaaatc    53820
aaatttagcc taaagctgcc tccttatata gtttaagctt gacctaaagg tttctctgta    53880
cttagtgaat tgtagcctac ccagatgtgt aaacaagact gtgaactact cttgtgacaa    53940
acattggatt ttgccaatc aaaggaggtc aactcttgac actgctttca ataaggcaa      54000 atattgagct gtaaacaatc tggctgtttc tatacctcac ttctgttttc tgtacgccac    54060
ttttctgtct ctgtccataa atgttcttcc accacgtggc tgtgctggag tctctgaacc    54120
tactctggct gaggaggctg cccaattctc aaactgttca attaaactcg gttaaattta    54180
atttgtctaa ggttttcttt taaccatata aacaagtgag tttatgattg ttatgtcttt    54240 tttctttct tttttgagac aaggtcccac tctgtccccc aggctggaat acagtggcat      54300
gatcacggct cactgtagtc tcgcactccc aggctcaagc gatcctccat ctcagcctcc    54360
tgagtagttg ggagtacaag tgcatgcaac catgcctggc taatttttt tttttttgta     54420 ttttttgtag agatagggtt ttgctacatt gcccaggttg atctcgaact cctgagctca    54480
agtgatcctc ttgcctcagc cttccaaagt gctgggacca caggcatgag tcaccacacc    54540
cagctattat ttctaaatta atgaacagat gaacattttc aaaatttctc agttttaatt    54600
```

```
ttaaatatga ttaaaaggat agatataaca cacaaacaaa agctctatgg agtcctctat    54660
aactcaagaa tataaagggt cctgagattt ttctttaaag agaaccactg cactctcctg    54720
gcctactagc tctccgcaat ccatcctgct tctcccttg  gcaggagaga cctgttctag    54780
accctcaagg acccctcata acatcaccta gctattatct aaggaatctt tctccatttg    54840
gacttcccat ttttttcttc ccccttaag  gtcccttat  tcttttcatc taattttgtg    54900
tgccacctgc agagtccttc ttcttcttct tctccttctc cttctccttc ttcttctcag    54960
agtcttgttc tgttgcccag gctggattgc agtggcacga tctcggctca cttcagcctc    55020
tgccttctgg gttccagtga ttctcctgcc tcaggctcct gggtagctgg gactacaggt    55080
acccaccatc atgactggct aattttttg  tattttagt  agagacgggg tttcacaatg    55140
ttagccagga tggtctctat ctcctgacct cgtgatccgg ccgcctcggc cttccaaagt    55200
gctgggatta caggcatgag ccaccgcacc cggcgactaa tttttttttt tttttttttt    55260
tttgagacgg agtctcactc tgtcgcccag gccggactgc ggactgcagt ggcacaatct    55320
cggctcactg caagctccgc ttcccgggtt cacgccattc tcctgcctca gcctcccgag    55380
tagctgggac tacaggcacc cgccaccgcg cctggctaat tttttgtatt tttagtagag    55440
acggggtttc accttgttag ccaggatggt ctcgatctcc tgacctcatg atccacccgc    55500
ctcggcctcc caaagtgctg ggattacagg cgtgagccac cgcgcccggc cggcgactaa    55560
tttttatatt tttagtagag acggggtttc gccatgttgg ctgggctggt cttgaactcc    55620
tgacctcagg tgatccgccc gccttggcct cccaaagtgt gggattaca  ggcatgagcc    55680 aacgcacccg gcctgagtcc tgcttcttcc agatctggtg cccagtcctg acgccagaaa    55740
gggggtcttg ttccagaccc caagagtgtt cttggatctt gcctgggaaa gaattcaggg    55800
taagtcgcag agtataatga agttaagata gttaattaga ggctactcaa ttacagagta    55860
gggcatcctc agaaaacaag aggaggaagg cgctacctta aatgtagtgc ttgcttatgt    55920
aggttgtata agaattgtgt actttattac aaaggcttgt gatcagcttg tgacaggcta    55980
ttggtactgt tattttcctg ttactattga tttcagcaag aatttatgag tacactatta    56040
tatttaaggc aaaacctatt ccttaagaat gcttttttgt cttaaaatac tgggacattt    56100
ccataagttc tgagtctta  gttagcaaca ttaactcatt ccctcaatca taaacatctc    56160
atgaccaaga gtgcccagtt cctggggaat gtaacccagc aggtttggct ttattcggcc    56220
tttattcaag atggagtcac tctggttagg acacctctga cagtccctgg aaatccaaag    56280
gaacccttct gtgtggcaca gggaatggaa gaaagaaaga gatgaggcag gaaaataggg    56340
tctggaggca gaaaacataa gccgattcac acttcagcta tgacaggaaa tatcctctcc    56400
atagggcgta tgcctgtaac tttacttcat cctcttcatt tacataggac gtatcctaag    56460
taaccaatgg aatcgtctag agggtattta aactcccaaa aattctgtaa cagggccttt    56520
gagcccctat gctcgggccc gctcccacac tgtggagtgt actttcattt tcaataaatc    56580
ccttcattcc ttccttgctt tctttgtgct ttgtgcattt tatctaattc tttgttcaag    56640
acgccaggaa cctggacgcc ctcccctggt aatagagaga tgagcctttc aaatgacctg    56700
actcctttat cccagccagg tgtgtgcccg accctgaaag gaggaatagg gaggggggacg    56760 ttcaacccgg cctcccgctc tgtgttagca gcgtctggat gggtcagggt ggaggtgggg    56820
gtgttctacc ctgctatttg ctcctagaga agcttctctg cttcactagt ctcacagttc    56880
taaaggcaag aacagcccta gtgggatctt ccaaggattt tagaaagaa  tgaataaggg    56940 aaaaattaaa atattgcagg gtgccataaa aacatcccag taaaacaaac acctttctag    57000
```

```
atgctcattg gaacgtaaat ggagctcagc ccccatccct tcacaccaga tccagtcttc    57060
atctttgtgg ttcactgccc cctcaccact caggaggaaa accccagctt ctgttctggc    57120
tccccttctc tcacttagaa ttttttcacca gagtttcaga aagatttgtc aggaccactc    57180
catgcccaag gtaaaaagtg taagtggtac aaaaaggtag aaactcatca gaccccaaa    57240 gagtgtcatt taaccataca aagccctgat aaactccagg gcagaagaaa aagctgcatc    57300
cttgactcca ctgggcatt cttatgtaaa ctaagatcca agaactgcat caggagagaa    57360
atcaagagcc ctggggatgt taggatgagc cctagaggtg ctaagacagg ttatttgaaa    57420
aaccaaaaag tagactgaga ttcccttcct tttcagggaa gaattgagac ctttcctttc    57480
ttactgttca gagtgggggc tgataagggt aattatttcc tggagccact ggctactgcc    57540
ctgggaagga aatccgctgg gttggggag ggaggaaggc agaaccaggc attaactctc    57600
cctccactac atcccttcc cgtacccctc ccctcctctc cttcccccca ctccctgccc    57660
ccgccctccg aaaatgacac ttggcctgag aaaggaggaa ggtagaatag gtggacactt    57720
cccttgtcct gctccagggg tgtctcagtg acaaggagat gtgaaaaaag aaggaatccc    57780
aaggctcccc ttggaaagaa gggagatctc caggggcttt gggaagtcag gttagtactg    57840
ggaaggctga agactcccag tagatagcgt tcagggctgc atttggctgc aatcctataa    57900
aatacattct tctctaaggt tggatacaag catttagaag actggccatt aaaaaaataa    57960
acagtattaa taatattaat aatcatgagt gtcagtagtg ttgaattttt tctggaatcc    58020
tttcccaagt tgcctaatgc ccagagaagg aaaataacag tgtttagtag acataaatta    58080
taggattagt gcaagtagct attgagatga tgagccaagg cttgtaaatt ggttttgttt    58140
tggttttcct aattagatgt ttgcgcctat ctgtgtatgt gtgtgtgtgt ttgtgcgtgt    58200
gcatgctcgc atgtggttaa tttcatgact tttgcctctg gctcttcctg attaaaaaaa    58260
atacttaaaa tggtaggaag tggcacacac ccttgatgga cctgtgttta tattaaagaa    58320
ttggcttagt aaatttaact gggacaagga aactgtgaag gactgtatt ttgccattat    58380 ttaataattc atatattcaa ccgttactga ttgcctattt tgaaccaggc cacgtgctag    58440
gatacaatgg ttaacaaaca cattccctcc cctcaaggaa ttcatggtct agtgaaatac    58500
agagatagaa aagaaataga aaagtatatc aataaaatgc attgtggaaa gagttatggt    58560
catagtgtgt actatatgct tatagaggct gcctttgtat aaacatacat aagactgctt    58620
tttaaattat aaaaggcagt acataggcca ggcgtggtgg ctcacacctg taatcccagc    58680
actttgggag gccgaggcgg gtggatcatc tgaggccacg agttcgagac cagcctggcc    58740
aacatggtga accccatttt ctactaaaaa tacaaaaaaa aaaaaaaaat tagccaggtg    58800
tggtggtggg cgcctcatcc cagctatcag gaggctgagg cggagaatc acttaaaccc    58860 agacggaggt tacagtgagc tgaggtggag ccattgcact ccagcctagg caacaagagc    58920
aaaactccat ctcaaaaaaa aaaaaaaaa aaaaaggca gtacatagta caaactgctt    58980
gggttttgtt gttgttgttt tactgtacca tataggttgg agatcattcc acctagtagc    59040
tgaacatttt aagcagatca tctggctaca ggcagtgagt aggatgaact gggagagtga    59100
tgagtgagtt agagagttag ggagggaggg tgctgtcgga gtgttaccgg aaaggggtcc    59160
cgatccacac cctaagagag ggttcttgga tctcgcacaa gaaagaattc agggcgagtc    59220
catacagtaa agtgaaagca gtttattaa gaaagtagag aaataaaaga atggctactc    59280
catagacaga gcagccccga gggctgctgt tgcccatttt tatggttatt ccttgatgat    59340
```

```
atgctaaaca agggtggat tattcatgcc tcccttttta gaccatatag ggtaacttcc   59400
tgacgttgcc atggcatttg taaactgtca tggcgctggt gggggcgtag tagtgaggat   59460
gaccagaggt cactctcgtg gccatcttag tgttggtagg ttttggccgg ctccaacacc   59520
ggcttgttgt tttatcagca aggtctttat gacccatatt ctatgcccac ctcctgtctc   59580
atcctgtgac ttagaatgcc ttaactgtct gggaatgcag cccagtaggt ttcagcctta   59640
ttttacccag ctcctattta agataaagtt gctctggttc acacgcctct gacaagaaca   59700
tcttcatgcc tgtgcctggt tgagagaggg aggcctctgc gctgctgctg gatctagtga   59760
agattcactc agtctctcaa attcctctac agtttctcta atggaagaga aaagtggtgt   59820
tattgctgct agggagcaac ctagaagtta ttttatttat gccatagata tggtgggcta   59880
agcactgtgc caacgttcaa taagtcactg cagattctcc ataaattatt gtgacaagta   59940
caattgtttg taaggcttag atctaggtgt gtaagtccaa agaagggtgt gaagcatctg   60000
tatttctgtt atgtagttat taggaaaaag gatgttgggg ccttaaaatg gccatttta    60060 acatttccaa acttgtgttg aattctaaga ttttataatt gtatgtttcc agttgagaag   60120
agctttgata ttggtagctc taaataaata aataccgttg acctggaaga gaaggtaaag   60180
tttagggaga ggccttttt tagctttata tttaaacatt ttttataaat gtgattcatg    60240
ggccaggcct ggtggctcac acctgtaatc ccagcacttt tggaggccaa tgcaggtgga   60300
tcacttgagg ctaggagttc gagagcagcc tggccaacat ggtaaaaccc catctctact   60360
aaaaattagc caggtgtggt agcacacacc tgtaatccca gctactcagg aggctgaggc   60420
aggggaatca cttgaaccca ggaggcgaag gttgcagtga ccgagattg tgccactgca    60480 ctccagcctg ggtgacagag tcagactccg tctcaaaagc aaaacaaaac aaaatgttat   60540
tcataatgct cggttgtaa ctatagtact tatctagcaa aagcttgctt tttttttt      60600 ggctttgact aattgaaact gcaagagctt actggcagag tggtgtactg gtcaatattt   60660
aaccaattct ccaaagggga aaaaccctga tttgtatgta ggatttgtca gtttccatgg   60720
tataaatagt cttcccacag ctggtagggt gaccaacttg ttctggtttg ccaggggctt   60780
tcccattttt aggcctgaaa gtcctgaatc cagaaaaatt cctcattccc caggaaaatag  60840 cttgattggt caccctaatg gctggttgca agctcccgat atgacagaac tggacgagaa   60900
gttgggcaga gatgtgcaca tggtaccagc ctatgccagg agcagcggcc tccagcaccc   60960
cactgtcagg gagtccttgg cccagtagag gatggttagc agggcccggc tgttgttcat   61020
attagctctc aaatttacca ccaaccctgt attagtttcc tggagctgct gtaacaaagt   61080
tccacaaacg ggggtcttaa acacagaaat ctattatctc acagttctgg agggcagaaa   61140
tagaaaatta aggtatgagc aggactctgc tcttttgatg gctctagata atccgttgta   61200
tgtcttttcc tcagcttctg gtttcacagg taatctttgg cgatccttga cttgcatctg   61260
tgtaactcca gtctctacct ccatcatcct gtggcattct tctttatttt tctttctttt   61320
tttcttttcg agacagagtt tcgctctgtt acccaggctg gagtgcagtg gcgtgatctc   61380
ggctcactgc aacctctgcc tcccaggttc aagcgattct cttgcctctg ctcccgagt    61440 agctgagatt acaggtgtgc gccaccacac ccagctaatt tttgcatttt tagtagaggc   61500 ggggttttcac catgctggcc aggctggtct cgggctcccg acctcaggtc atctccctgc   61560
cttggccttc taaagtgctg ggattacaag cgtgagccac tgcactcggc ccatggcatt   61620 cttctttttgg tgcctttgtc ttcactgact tcttgtaagg aaatcagtcg tattggatta   61680
gaggcctacc ttattccagt atgatctcat tgtcttaatt taactaaaac atctgcaaca   61740
```

```
accttattc taaatgaggt cacattctga ggtattaggg tttagtactt caacatatct   61800
tttttttttt tttgagacag ggtctcattc tgtcactcag gctggagtgc agtggtgcaa   61860
tcacacagct cactgtaact ttgaactcct gggctcgagc agtcctccta tctcagcctc   61920
ccagataggt aagattacag gtacatatca ccatgcctag ctaattttc aaatttttta   61980 taggggctgg gcccagtggc tcacaccttg taatccctgt aatcccaaca ctttggtagg   62040
ctgaggcggg cggatcactt gaggtcaaga gtttgagacc agcctggcca acatggtaaa   62100
atcccatctc tactaaaaaa aatacaaaaa ttagccggat gtggtggtgg gtacctatca   62160
taccagctac tcacaaggct gaggccggaa aatccctgga acccgagggg cggagatcgc   62220
agtgaaccga gatcacgcca tgcactccag cctgggtgac agagcaagac ataaccttaa   62280
aaaagaaaaa aaaaaatgta gagatgaagt cttgctgtgt tgcccaggct agtctcaaat   62340
gcctgggctc aagcaatcct tctgcctcag tatcccaaag tgctaggatt acaggcatga   62400
ggcactgcac caggcctaca tcctcttttt ttttttttt tttttttttt tttgagatag   62460
agtcttgctc tgtctcccag gctggagtgc agtggcacga cctcggctca ctgcaacttc   62520
cacctcctgg gttcaagtga ttcttctgcc tcagcctcca gagtagctaa gactacaggc   62580
ataatatctc tcttagatat gacaaataat atcacagagt gtacacccac tgtgatgtta   62640
ggagtaatac ctccctatga tattacaagt aatactgcct ttagatacta caaataatat   62700
cacagggtgt acatctactg tgatattagg agtaatacct cccttagata ttacaaataa   62760
tatcacaggg tatacacca cggtgatatt aggagtaata tctctcttaa gcgatcctcc   62820
catctcagcc tcacagaatt aaaggaatta caggaagagc tgctatacct ggctggatct   62880
atgttttaaa aatataaccc agataaccct gtggtcagtg tctaagatga attggattag   62940
accaagggag aaaaactaaa gatgggaata ctagtttggg actttgcttg cttgcttgct   63000
ctcatttaga aaacatttag tagttctaca atgctcaggc actgttctgg gagtcacaaa   63060
tataggattg aataaagtaa ataaagcact tgctctcctg gagctcactt ttcactgggg   63120
gaatgcagat agtagacaca tacatctata gtatcagtaa gtgctaatag aaaaatgaag   63180
caggtgagat ggatcatgct gagtagaatg tatcttcttt tccttccttc cttccttccc   63240
tccctccttc cttctttcct tccttctttc tttccttcct ttcttctttt ctctttcttc   63300
ctttctctct ctttctttgc tttttattgt cttaaaatgt acataacata aaatttaccc   63360
tcttaaccat ttttaagaat acaattcaag gccgggcatg gtggctcaca cctataatcc   63420
cagcattttg ggaggctgag gcaggcggat catgaggtca ggagtttgag gccagtctgg   63480
ccaatatgat gaaaccccat ctctactaaa aaatacaaaa attagccagg cttggtggca   63540
catgcctgta gtcccagcta cccgggaggc tgaggcagga gaatagctgg aacctgggag   63600
gcagaggttg cagtgagctg agatcgcacc actgcactcc tgcctggaca agagagcaag   63660
actctgtctc aaaaataaat aaataaataa ataataataa taataataat acaattcagt   63720
agccttaagt acatttgcat tgttatgcag ccatcaccac catccatctc cagaattttt   63780
ttgagtggag ctctttttaa tagagtagtt gaaggcctct gtgacacagt agcatctgag   63840
cagaagcttg aatgaagtga gaaaagaatc cttttgcata gtttagggga agtatgttcc   63900
attcctggtc ctggaaatag ttaagactat cacaatagtg caggagaaag atgatacaat   63960
acagtttgtg tagctgaaac cccgtcttca gaatgtaaag gagaacagat gggaagtcat   64020
gttcctccca gaagtaattc atgtagcaga gaagccaatg cagatccacg agacagacaa   64080
```

```
ttcagtgctc tgcacaagaa ctgtgcttta agcatggaga ggattttgt atctgtcctg    64140 ggatcctaca tcaaacagca tgtggtgatt gtgaacacaa acgtacaaga ctgtgaaccc    64200
taccaagttt ccttcttcca ttagatatga ataaggagtc atgagtttcc tttggaatgt    64260
cctttagcct gttggtacat gttttgcctg tgacgaatgc agttactcat aaatcattga    64320
gcacattggg tacagagggc aaaagataaa ttcctgtatt tcctctattc ggtcaacaga    64380
aatacctcta ggccataatc cattcatcca atctaataat tttgccatcc ataaaacctt    64440
caggtgttct gaattcaaca tctttttttt ttttttttt tttttttgag acagagtctt    64500
gctctgtcac ccaggctgga gtgcaatggc aggatctcgg cttactgcaa cctccgcctc    64560
ccagattcaa gcgattctcc tgcctcagcc tcccgagtag ctgggattac aggtgcccgc    64620
caccacgccc agctaatttt ttgtattttc agtagagacg gggtgtcacc atgttggcca    64680
ggctggtctc gaactcttga cctcaggcaa tccacccgcc tcagcctccc aaagtgctgg    64740
gattacaggc gtgagccacc atgcctggct gaattcgaca tcttgcacct aattcctgtt    64800
cagttaaaga cccaaatcat gatctctgac ttacctggat atttgaaaga ttaacttgct    64860
gtggtgatac catactagag tcacaaaatc aagccctacc ctgccacagc cacctaaagg    64920
aaattaggtg atatacaaaa gaaattgacc atattgttgt ccttttagtg actctcctaa    64980
ttttcttccc ctgaaaactt acagagaaat ttgagtatgt ttgccttagg tggatgcttg    65040
tttttttatt gatatgaaaa gcagtaagag gaaatggagt tttttggcct gttaaggaag    65100
ggcagccact gtaaacacag ttgagtgcaa attcacagtg ttagaatgtt gaagtgtata    65160
taatgatttt gcaaaatttt ctacaaggct gatacagtat ccaatcagga ctaggattag    65220
atatattgtc atgtatgttt gcgcaggaaa tgcagagact ctaaggtgct acaactgcaa    65280
tttgacatgt gggatagttc actggtaact gttgatctcc ctgaggttta agtttacagt    65340
tccacagctc tttatctgaa actcttgggc tatgtgttat ggaatttaga atttttccg    65400 aaatacgttg catatattgt atattatgac atgataccct caagaaagac ttggagtcac    65460
atcctataaa caaacacatg aatatatccc agtgaaatgt atgactattt ttactaaaac    65520
aaatgagaat cataaataga cttacattac ttcaggtcag atttgctgc cgaattagtt    65580 tgggcatcga acttttggtt tcagagacaa aactgtgaaa ttttagatta tattatgggg    65640
ttgtggaccc atgtaaccct cctctccgta attcctaaaa gcaagcaatt gcatcaacca    65700
gtctcatgag tagctgcgat tctagaaatc aagaatccgg atctgaaatt agccgggcat    65760
ggtggcaggc acttgtaatc ccagctactg ggaggctga ggcaggagaa tcgcttgaac    65820
ccaggaggaa actgcagtga gctgagatcg tgctgctgca ctccagcctg gcaacagag    65880 tgagactctg tctcaaaaaa aaaaaaaaaa aaaaaaaag aatccagatc tgggcaggac    65940
cgaattgctg acatgccccc ggtatagcag agacgttttg cctacatgtt acacacctga    66000
gtaatagttg tcagcagctg atgaagaaga tgaatgtgct cttaatgtcc atctttgatt    66060
tccagtcatt ttgcttctgg gtcttggctt cctgaggaaa gaagtctcca gtaggtgaat    66120
gcagtgatat ggagaatact ttcttctggc tgcatgcagt aactcacacc tgtaatccca    66180
gcacattggg aggctgaggt gggcagtgca cttgaggttg ggagttcgag accagcctgg    66240
ccaacatggc aaaccccgt ctctactgaa aatacaaaaa ttagctgggc gtggtgacag    66300
acacctgtca tcccagctac tcggtaggct gaggcatgag aatcacttga acttgggagg    66360
tagaggttgc agtgagccga gatcgtgcct ctgcactcca gctgggcaac acagcgagac    66420
tctgtctcaa aaaaaaaaaa gtgtgtgaga gagagtactt tcttcctgtt tcctcatagg    66480
```

```
ccagttctct ctggcatgtg agtttaacat cagtcacctc cttcacacac agcgggtgca   66540
ttcgtaatag gaggtcctta gctgggagtt tttatggcac atcagtgggg cgtgaaaaca   66600
ccacatagga gctaatatat ctttgctggc tgctttctcc ggctccgcag cagacagaaa   66660
ccctatgaat catatccagg ggtcaggtgc aggcaacaga caactaatat ctcccaagtg   66720
agttgaaaag gatcttgtta cccagcatcc taaggaggtt gtagccttgg gaaccacagg   66780
caagaataat taactcagct cctcggttag tgcctcttca gttcgagatg gaatttattt   66840
gcaggcatgg ctccttaata tgccaaaccc atgctcaaga catactcctt ctcctggaag   66900
gttaacgtgg ctcctgtggc tgttccatcc ctgaggaaaa gtgaggacca tgctctccaa   66960
acaggccatg tgctggacta cctctgtttc tgtctcctgg gattccaatc agcaagtgag   67020
caacgaagca acccagacag tgtggttcat aggatggctg ggtaagtggc tgtttgtttt   67080
ttccttactg tggatatgta tcagtgaagg aatctgtaga acattcttga tgggaacatt   67140
tagtcatatc aagtcaataa attaatgttt aggctgggcg cagtggctca cgcctgtaat   67200
cccaacacct gggaggcca aggcgggcag atcatctgag gtcaggagtt caagaccagc   67260
ctggccaaca tggtaaaatc ccgtctctac taaaaataca aaaattagct gggtgtggtg   67320
gtgcatactt gtagtcccag ctactctgga ggctgaggca agagaattgc ctgaacctgg   67380
gagatggagg ttgcagtgag ctaagagtgc accattgcac tctagcctgg caacagagt   67440 gagactctgt caaaaaaaaa ttaaaaaaaa agaaaaatca ttatttatt tttgacttat   67500 tattaatata aataattata tcttggccgg gcatagtgtc tcatgcctat aatcccagca   67560
ctttgggagg ccagggcagg cagatcactt gagccaagaa gtttaagacc agcctgggca   67620
acacggtgaa accctgtctc tacaaaaaat ataaaaaatt agctgggagt ggtcagcttg   67680
cctgcagccc tagctacctg ggaggctgag gtgggaggat cacctcggcc caggaggtag   67740
aggctgcagt gagccatgat tgtaccactg cactccagcc tgggtgatag agtgatgaga   67800
ccctgtctca aaaaaaaaa aaaaaaaaa aagaaagaaa gaaagaaaaa agaaaggaaa   67860
agaaatcata tattggtgag gagacaattc aacacatatt ttttattgaa cacatactat   67920
gtgtcagggt accagatata agctctatct acaaggattt taggagctgg agtatgtgta   67980 tgggggatg tatgagtgtg tataacaaag acgactcctg gggaagaaga ggaagacaag   68040
ccccagaggt atactgcata ggcataatac acaacaggct agcaaagaag caaaccatgg   68100
gtatggtaga gagaatcaga ggatacattg gggaccatgt ctagtgagtg aggtcaggag   68160
agacttcaat aatctgagtg aatttagaca tgggccttga aaagtggaca aggtttgttg   68220
ttgttgttgt tgttgttgtt gttgttgttg ttgttgttgt ttttgagatg gagtctcatt   68280
ctgtcgccca ggctggagtg cagtggtgcg atctcggctc actgcaagct ccgcctccca   68340
ggttcataac attctcctgc ctcagcttcc cgagtagctg ggactacagg cgcccgccac   68400
cacgcccagc tactttttta tattttagt agagacgggg tttcaccgtg ttagtctgga   68460
tggtctcgat ctcctgacct tgtgatccac ccaccttggc ctcccaaagt gctgggatta   68520
caggcgtgaa ccactgcggc cggcctaaat ttgttttaaa agtacgcata ggaaggctgg   68580
gggctgtggc ttatgcctgt aatcacagca ctttgggagg ccaagacagg cagatcacga   68640
ggtcaggaga tcgagaccat cctggctaac acagtgaaac cccgtctctc caaaaaaaca   68700
aaaaattatc caggcctagt ggcacacgcc tgtagtccca gctacttggg aggctgaggc   68760
aggagaatcg cttgaatctg ggaggtggag ggtgcagtga gccactgcac tccagcctgg   68820
```

```
gtgacagagc aaactaggtc tcaaaaaaaa aaaaaaaaaa aagtacatgt gggggacagg    68880
tgcagtgtct cagcctgtaa tcaatcccag cactttggga ggctgaggtg ggtggatcac    68940
ttgaggtcag gagttcaaga ccagcctggc aacatggag aaaccccatc tctactaaaa    69000
atacaaaaat tcgctgggcg tggtggcgca cgtctgtagt cccagctact gggaagacta    69060
aagtgagaga actgcttgag cccagaggtc gaggctgtgg tgagcggtga tttcaccact    69120
tcagtctagc ctgggtgaca gagagagacc ctgtctcata taaacaaata aataaaagtt    69180
tatttattta ttacacatat ttattacaca ttattacaag accttgaact aacaacatta    69240
acatgcattt gttaaaggaa aataaattag ctcagatgct actactttc ataatacttg    69300 cacgattgat ttcaatccct gttcatctga atggagagtt gcaggtatac tatgcagcta    69360
ttctacttat attctgtttt ttaatgtaac agtattattt cttgatgtct ctacacattt    69420
tatatcactt taatatttaa taaaaacatc taccataagt tctaaaatgg taaaggaag    69480 aatagtcatt agtactgtca ctaccctgaa tgaatacaaa tacagtttgc actagggctt    69540
attttgctcc tgtcctttgc ctgtgcattt catttttgca tcgtggtaat catactgggt    69600
gaattttgta ttctgtaatt tcaactgaat attatatcat aagtgttatc tacaagttcc    69660
atgaggacca aatcttctcc accttttca ccatttact tagcatggta tagtaaagct    69720
ggctcaataa atatttgctg attgaataaa tgttgttaca tgctcttcct gattaacata    69780
tatatacgca tatacaattt tttagtgact gcattaattt acttcatttt ttcctaattg    69840
ttggatattt cagttgccat ttttttgctt ttatgaataa tgtgttgatg aaaagatttg    69900
tgcatatagt tttctctgca tttggactat tgtcttttt ttttttttta aagatagagt    69960
cttgtgctgt cactcaggct gcaatgcagt ggcgcaatct                          70000

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2
cttcttcttc ttcttc                                                    16

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
tcttcttctt cttctt                                                    16

<210> SEQ ID NO 4
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 4
ttcttcttct tcttct                                                    16

<210> SEQ ID NO 5
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 5
ttcttcttct tcttcttc                                                     18

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
cttcttcttc ttcttctt                                                     18

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
tcttcttctt cttcttct                                                     18

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
tcttcttctt cttcttcttc                                                   20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ttcttcttct tcttcttctt                                                   20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
cttcttcttc ttcttcttct                                                   20

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
```

-continued

<223> OTHER INFORMATION: bases at these positions are RNA

<400> SEQUENCE: 11
tuucuucuaa aucuucuuca a                                             21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 12
tcuucuucaa auucuucuua a                                             21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 13
tucuucuuaa acuucuucua a                                             21

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 14
tuucuucuuc uucuucuuca a                                             21

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 15
tcuucuucuu cuucuucuua a                                             21

<210> SEQ ID NO 16
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature

```
<222> LOCATION: (2)..(21)
<223> OTHER INFORMATION: bases at these positions are RNA

<400> SEQUENCE: 16
tucuucuucu ucuucuucuu aa                                              22

<210> SEQ ID NO 17
<211> LENGTH: 23
<212> TYPE: DNA
<213> ORGANISM: Artificial sequence
<220> FEATURE:
<223> OTHER INFORMATION: Primer

<400> SEQUENCE: 17
aagccataca cgtttgagga cta                                             23

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
ttggcgtctg cttgttgatc a                                               21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gccaatatca taacccaagc                                                 20

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: n is a, c, g, or t

<400> SEQUENCE: 20
nnnnnnnnnn nnnnnn                                                     16

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: n is a, c, g, or t

<400> SEQUENCE: 21
nnnnnnnnnn nnnnnnnn                                                   18

<210> SEQ ID NO 22
<211> LENGTH: 21
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: n is a, c, g, or t

<400> SEQUENCE: 22
nnnnnnnnnn nnnnnnnnnn n                                              21
```

MODULATION OF FRATAXIN EXPRESSION

This application is a national phase application under 35 U.S.C. § 371 of International Application No. PCT/US2018/067087, filed Dec. 21, 2018, which claims benefit of priority to U.S. Provisional Application U.S. Ser. No. 62/609,056, filed Dec. 21, 2017, the entire contents of each of which are hereby incorporated by reference.

STATEMENT OF GOVERNMENT SUPPORT

This invention was made with government support under Grant No. GM R35118103 awarded by the National Institutes of Health. The Government has certain rights in the invention.

SEQUENCE LISTING

The present application is being filed along with a Sequence Listing in electronic format. The Sequence Listing is provided as a file entitled IONSP0008US_ST25.txt created on Jun. 19, 2020, which is approximately 95 KB in size. The information in the electronic format of the sequence listing is incorporated herein by reference in its entirety.

FIELD

Certain embodiments are directed to methods and compounds for upregulating FXN protein. Such methods and compounds are useful for inducing expression of FXN in cells and animals.

BACKGROUND

Friedreich's Ataxia (FA) is an incurable disease caused by an expansion of a trinucleotide GAA repeat within intron 1 of the frataxin gene (FXN). This expansion does not change the coding region of FXN and does not result in expression of a mutant protein. Instead, the gene mutation reduces expression of FXN protein. Agents that increase expression of FXN protein to restore it to normal levels would have the potential to be a therapy for FA.

While the mechanism linking expansion of the trinucleotide repeat to reduced expression of FXN is not known with certainty, evidence suggests that the expanded intronic RNA forms an RNA loop (R-loop) with chromosomal DNA that induces histone and possibly DNA modification to act as a break on transcription. Compounds that bind the expanded repeat would be expected to block the expanded RNA, inhibit recognition of DNA, prevent R-loop formation, and allow increased expression of FXN.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

SUMMARY

Several embodiments provided herein relate to the discovery that modified oligonucleotides targeting the GAA trinucleotide repeat expansion in FA increase expression of FXN. Several embodiments are drawn to methods and compounds for inducing expression of FXN using modified oligonucleotides targeting the GAA trinucleotide repeat. Certain embodiments disclosed herein are drawn to a method of inducing expression of FXN in a cell comprising contacting the cell with a modified oligonucleotide targeted to the GAA trinucleotide repeat. In certain embodiments, modified oligonucleotides described herein increase expression of FXN protein in a cell. In certain embodiments, modified oligonucleotides described herein increase expression of FXN protein in a cell, but do not substantially alter the amount of FXN pre-mRNA in a cell. In certain embodiments, FXN comprises a nucleic acid sequence at least 85% identical to SEQ ID NO: 1.

The present disclosure provides the following non-limiting numbered embodiments:

Embodiment 1: A compound comprising a modified oligonucleotide 8 to 80 linked nucleosides in length having a nucleobase sequence comprising at least 16 contiguous nucleobases of any of the nucleobase sequences of SEQ ID NOs: 2, 3, 4, 5, 6, 7, 8, 9, 10, 11, 12, 13.

Embodiment 2: A compound comprising a modified oligonucleotide 8 to 80 linked nucleosides in length having a nucleobase sequence comprising the nucleobase sequence of any one of SEQ ID NOs: 2, 3, 4, 5, 6, 7, 8, 9, 10, 11, 12, 13.

Embodiment 3: A compound comprising a modified oligonucleotide having a nucleobase sequence consisting of any one of SEQ ID NOs: 2, 3, 4, 5, 6, 7, 8, 9, 10, 11, 12, 13.

Embodiment 4: The compound of any one of embodiments 1-3, wherein the modified oligonucleotide comprises at least one modified internucleoside linkage, at least one modified sugar, or at least one modified nucleobase.

Embodiment 5: The compound of embodiment 4, wherein the modified internucleoside linkage is a phosphorothioate internucleoside linkage.

Embodiment 6: The compound of embodiment 3 or 4, wherein the modified sugar is a bicyclic sugar.

Embodiment 7: The compound of embodiment 6, wherein the bicyclic sugar is selected from the group consisting of: 4'-(CH2)2-O-2' (ENA); and 4'-CH(CH3)-O-2' (cEt).

Embodiment 8: The compound of embodiment 4 or 5, wherein the modified sugar is 2'-O-methoxyethyl.

Embodiment 9: The compound of any one of embodiments 4-8, wherein the modified nucleobase is a 5-methylcytosine.

Embodiment 10: The compound of any one of embodiments 1-9, wherein the compound is single-stranded.

Embodiment 11: The compound of any one of embodiments 1-9, wherein the compound is double-stranded.

Embodiment 12: The compound of any one of embodiments 1-9, wherein the modified oligonucleotide consists of 16 to 30 linked nucleosides.

Embodiment 13: The compound of any one of embodiments 1-9, wherein the modified oligonucleotide consists of 16 to 22 linked nucleosides.

Embodiment 14: The compound of any one of embodiments 1-9, wherein the modified oligonucleotide consists of 16 to 20 linked nucleosides.

Embodiment 15: The compound of any one of embodiments 1-9, wherein the modified oligonucleotide consists of 16 to 18 linked nucleosides.

Embodiment 16: The compound of any one of embodiments 1-9, wherein the modified oligonucleotide consists of 16 linked nucleosides.

Embodiment 17: The compound of embodiment 16, wherein the modified oligonucleotide has a nucleobase sequence consisting of any one of SEQ ID NOs: 2, 3, or 4.

Embodiment 18: The compound of embodiment 17, wherein each sugar is a modified sugar.

Embodiment 19: The compound of embodiment 18, wherein each modified sugar is a 2'-methoxyethyl sugar.

Embodiment 20: The compound of embodiment 17, wherein the sugar motif is (edd)5-e, where e represents a 2'-methoxyethyl modified nucleoside and d represents a 2'-deoxy nucleoside.

Embodiment 21: The compound of embodiment 17, wherein the sugar motif is (kdd)5-k, where k represents a 2'-cEt modified nucleoside and d represents a 2'-deoxy nucleoside.

Embodiment 22: The compound of embodiment 17 or 18, wherein the sugar motif is (kee)5-k, where k represents a 2'-cEt modified nucleoside and e represents a 2'-methoxyethyl modified nucleoside.

Embodiment 23: The compound of any of embodiments 17-22, wherein each internucleoside linkage is selected from phosphorothioate and phosphodiester.

Embodiment 24: The compound of any of embodiments 17-23, wherein each internucleoside linkage is phosphorothioate.

Embodiment 25: The compound of any one of embodiments 1-9, wherein the modified oligonucleotide consists of 18 linked nucleosides.

Embodiment 26: The compound of embodiment 25, comprising a modified oligonucleotide having a nucleobase sequence consisting of any one of SEQ ID NOs: 5, 6, or 7.

Embodiment 27: The compound of embodiment 25 or 26, wherein each sugar is a modified sugar.

Embodiment 28: The compound of embodiment 27, wherein each modified sugar is a 2'-methoxyethyl sugar.

Embodiment 29: The compound of embodiment 25 or 26, wherein the sugar motif is e-(edd)5-ee, where e represents a 2'-methoxyethyl modified nucleoside and d represents a 2'-deoxy nucleoside.

Embodiment 30: The compound of embodiment 25 or 26, wherein the sugar motif is k-(kdd)5-kk, where k represents a 2'-cEt modified nucleoside and d represents a 2'-deoxy nucleoside.

Embodiment 31: The compound of embodiment 25 or 26, wherein the sugar motif is k-(kee)5-kk, where k represents a 2'-cEt modified nucleoside and e represents a 2'-methoxyethyl modified nucleoside.

Embodiment 32: The compound of any of embodiments 25-31, wherein each internucleoside linkage is selected from phosphorothioate and phosphodiester.

Embodiment 33: The compound of any of embodiments 25-31, wherein each internucleoside linkage is phosphorothioate.

Embodiment 34: A compound comprising a modified oligonucleotide having a nucleobase sequence consisting of any one of SEQ ID NOs: 8, 9, or 10.

Embodiment 35: The compound of embodiment 34, wherein the modified oligonucleotide is a phosphorodiamidate morpholino oligomer (PMO).

Embodiment 36: A compound comprising a single-stranded oligonucleotide consisting of 13 to 30 linked nucleosides and having a nucleobase sequence complementary to a repeat region of an expanded repeat-containing target RNA, wherein the 5'-terminal nucleoside of the single-stranded oligonucleotide comprises a stabilized phosphate moiety and an internucleoside linking group linking the 5'-terminal nucleoside to the remainder of the oligonucleotide.

Embodiment 37: The compound of embodiment 36, wherein the single-stranded oligonucleotide has a nucleobase sequence comprising at least 16 contiguous nucleobases of any of the nucleobase sequences of SEQ ID NOs: 14, 15, or 16.

Embodiment 38: The compound of embodiment 36, wherein the single-stranded oligonucleotide has a nucleobase sequence consisting of any one of SEQ ID NOs: 14, 15, or 16.

Embodiment 39: The compound of any of embodiments 36-38, wherein the 5'-terminal nucleoside has Formula I:

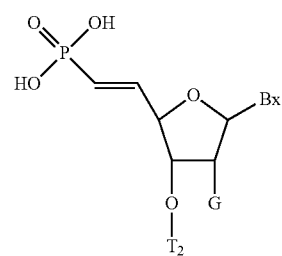

wherein:
Bx is selected from among: uracil, thymine, cytosine, 5-methyl cytosine, adenine, and guanine;
$T_2$ is a phosphorothioate internucleoside linking group linking the compound of Formula I to the remainder of the oligonucleotide; and
G is selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—$N(H)$—$(CH_2)_2$—$N(CH_3)_2$, $OCH_2$—$N(H)$—$C$(=$NH$)$NH_2$, and a conjugate group.

Embodiment 40: The compound of any of embodiments 36-37, comprising the motif:

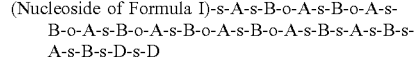

wherein:
s is a phosphorothioate linkage;
A is a nucleoside of a first type;
B is a nucleoside of a second type; and
D is a nucleoside of a third type.

Embodiment 41: The compound of any of embodiments 36-37, consisting of the motif:

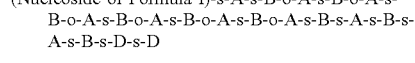

wherein:
s is a phosphorothioate linkage;
A is a nucleoside of a first type;
B is a nucleoside of a second type; and
D is a nucleoside of a third type.

Embodiment 42: The compound of embodiment 40 or 41, wherein A is a 2'-F nucleoside.

Embodiment 43: The compound of any of embodiments 40-42, wherein B is a 2'-OMe nucleoside.

Embodiment 44: The compound of any of embodiments 40-43, wherein D is a 2'-MOE nucleoside.

Embodiment 45: A compound consisting of a pharmaceutically acceptable salt of any of the compounds of embodiments 1-44.

Embodiment 46: The compound of embodiment 45, wherein the pharmaceutically acceptable salt is a sodium salt.

Embodiment 47: The compound of embodiment 45, wherein the pharmaceutically acceptable salt is a potassium salt.

Embodiment 48: A composition comprising the compound of any one of embodiments 1-47 and a pharmaceutically acceptable carrier.

Embodiment 49: A composition comprising a compound or modified oligonucleotide of any preceding embodiment, for use in therapy.

Embodiment 50: A method of treating, preventing, or ameliorating a disease associated with frataxin in an individual comprising administering to the individual a compound targeted to the repeat of frataxin thereby treating, preventing, or ameliorating the disease.

Embodiment 51: The method of embodiment 50, wherein the disease is Friedreich's Ataxia.

Embodiment 52: The method of any of embodiments 50-51, wherein administering the compound inhibits, reduces, or improves the symptoms of Friedreich's Ataxia.

Embodiment 53: A method of increasing expression of frataxin in a cell comprising contacting the cell with a compound targeted to the GAA repeat of frataxin, thereby increasing expression of frataxin in the cell.

Embodiment 54: The method of embodiment 53, wherein the cell is in the CNS of an individual.

Embodiment 55: The method of embodiment 54, wherein the individual has, or is at risk of having, Friedreich's ataxia.

Embodiment 56: The method of any one of embodiments 50-55, wherein the compound is the compound of any one of embodiments 1-47 or composition of any of embodiments 48 and 49.

Embodiment 57: The method of embodiment 55 or 56, wherein the compound is administered to the CNS.

Embodiment 58: Use of a compound targeted to frataxin in the manufacture of a medicament for treating, preventing, or ameliorating a disease associated with frataxin.

Embodiment 59: The use of embodiment 58, wherein the compound is the compound of any one of embodiments 1-47 or composition of embodiment 48 or 49.

Embodiment 60: Use of a compound targeted to frataxin in the preparation of a medicament for treating, preventing, or ameliorating a disease associated with frataxin.

Embodiment 61: The use of embodiment 60, wherein the disease is Friedreich's ataxia.

Embodiment 62: The use of embodiment 58 or 60, wherein the compound is an antisense compound targeted to frataxin.

Embodiment 63: The use of any one of embodiments 58-62, wherein the compound is the compound of any one of embodiments 1-47 or composition of any of embodiments 48 and 49.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO described herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Compound Number (Compound No) indicate a combination of nucleobase sequence and motif.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, FXN means frataxin-1. In certain embodiments, FXN transcript comprises GenBank accession NC_000009.12 truncated from 69033001 to 69103000.

As used herein, "Frataxin-1 (FXN)" means any FXN nucleic acid or protein. "FXN nucleic acid" means any nucleic acid encoding FXN. For example, in certain embodiments, a FXN nucleic acid includes a DNA sequence encoding FXN, an RNA sequence transcribed from DNA encoding FXN, including a non-protein encoding (i.e. non-coding) RNA sequence, and an mRNA sequence encoding FXN. "FXN mRNA" means an mRNA encoding a FXN protein.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —$OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "phosphordiamidite morpholiono oligomer" or "PMO" means an oligomer comprising subunits having the following structure:

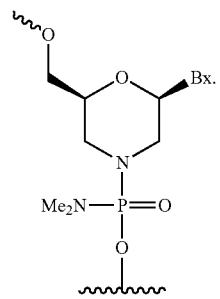

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid.

Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2' bridge.

As used herein, "locked nucleic acid nucleoside" or "LNA" means a nucleoside comprising a bicyclic sugar moiety comprising a 4'-$CH_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-mRNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)

$_2N(R_{bb})(R_{cc})$ or $—N(R_{bb})S—(O)_2R_{bb})$. Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula $—C(O)—X$ where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage. In certain embodiments, an oligomeric compound consists of a phosphorodiamidite morpholino oligomer.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

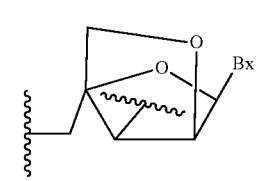

(A)

(B) 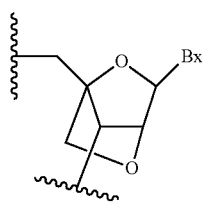

(C) 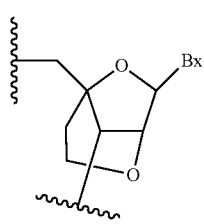

(D) 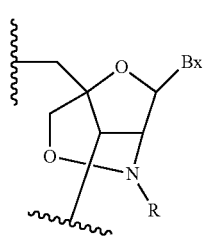

(E) 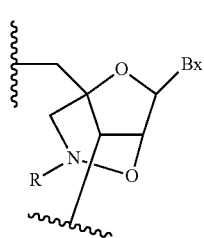

(F) 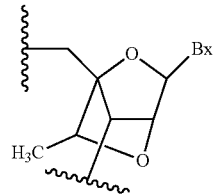

(G) 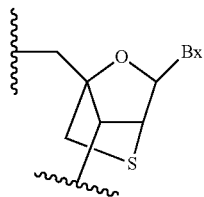

(H) 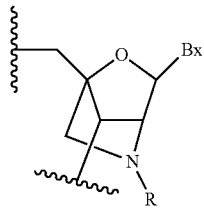

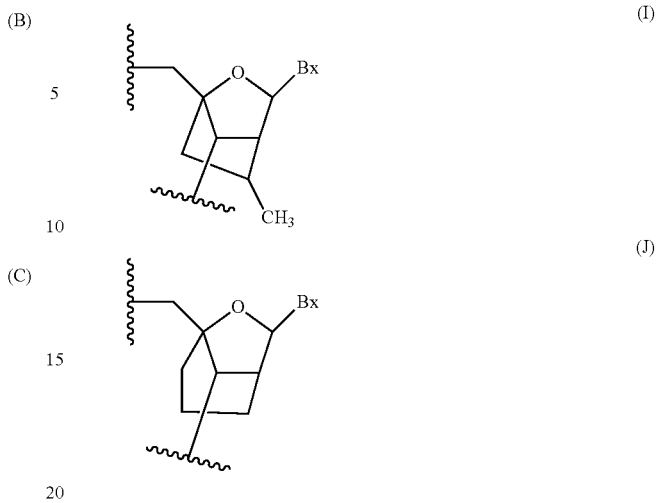

wherein Bx is a nucleobase moiety and R is, independently, H, a protecting group, or $C_1$-$C_{12}$ alkyl.

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. Patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. &Med. Chem.* (2002) 10:841-854), fluoro HNA (F-HNA), and those compounds having Formula VII:

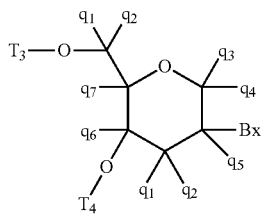

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)$ $NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

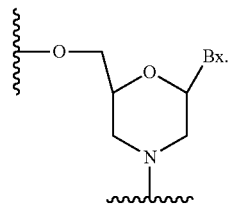

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2- one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

In certain embodiments, the oligonucleotides of the present invention comprise sugar modification and backbone motifs selected from the table below. In certain embodiments, oligonucleotides comprising sugar modifications and backbone motifs selected from the table below are particularly effective at increasing expression of FXN in a cell.

| Sugar Motif | Length | Backbone Motif | Chemical Notation | SEQ ID NO |
|---|---|---|---|---|
| e16 | 16 | full PS | $N_{es}N_{es}N_{es}N_{es}N_{es}N_{es}N_{es}N_{es}$ $N_{es}N_{es}N_{es}N_{es}N_{es}N_{es}N_{es}N_{e}$ | 20 |
| (edd)5-e | 16 | full PS | $N_{es}N_{ds}N_{ds}N_{es}N_{ds}N_{ds}N_{es}N_{ds}$ $N_{ds}N_{es}N_{ds}N_{ds}N_{es}N_{ds}N_{ds}N_{e}$ | 20 |
| (kdd)5-k | 16 | full PS | $N_{ks}N_{ds}N_{ds}N_{ks}N_{ds}N_{ds}N_{ks}N_{ds}$ $N_{ds}N_{ks}N_{ds}N_{ds}N_{ks}N_{ds}N_{ds}N_{k}$ | 20 |
| (kee)5-k | 16 | full PS | $N_{ks}N_{es}{}^mN_{es}N_{ks}N_{es}{}^mN_{es}N_{ks}N_{es}$ ${}^mN_{es}N_{ks}N_{es}{}^mN_{es}N_{ks}N_{es}{}^mN_{es}N_{k}$ | 20 |
| e18 | 18 | full PS | $N_{es}N_{es}N_{es}N_{es}N_{es}N_{es}N_{es}N_{es}$ $N_{es}N_{es}N_{es}N_{es}N_{es}N_{es}N_{es}N_{es}N_{e}$ | 21 |
| e-(edd) 5-ee | 18 | full PS | $N_{es}N_{es}N_{ds}N_{ds}{}^mN_{es}N_{ds}N_{ds}{}^mN_{es}$ $N_{ds}N_{ds}{}^mN_{es}N_{ds}N_{ds}N_{es}N_{ds}N_{ds}N_{es}N_{e}$ | 21 |
| k-(kdd) 5-kk | 18 | full PS | $N_{ks}N_{ks}N_{ds}N_{ds}N_{ks}N_{ds}N_{ds}N_{ks}N_{ds}$ $N_{ds}N_{ks}N_{ds}N_{ds}N_{ks}N_{ds}N_{ds}N_{ks}N_{k}$ | 21 |
| k-(kee) 5-kk | 18 | full PS | $N_{ks}N_{ks}N_{es}N_{es}N_{ks}N_{es}N_{es}N_{ks}N_{es}$ $N_{es}{}^mN_{ks}N_{es}N_{es}{}^mN_{ks}N_{es}N_{es}N_{ks}N_{k}$ | 21 |
| e-(fm) 9-ee | 21 | s-(so) 6-s7 | $N_{es}N_{fs}N_{mo}N_{fs}N_{mo}N_{fs}N_{mo}N_{fs}N_{mo}$ $N_{fs}N_{mo}N_{fs}N_{mo}N_{fs}N_{ms}N_{fs}N_{ms}N_{fs}$ $N_{ms}N_{es}N_{e}$ | 22 |

A subscript "d" indicates an unmodified, 2'-deoxy sugar moiety. A subscript "e" indicates a 2'-methoxyethyl modification. A subscript "k" indicates a cEt modification. A subscript "s" indicates a phosphorothioate internucleoside linkage, while a subscript "o" indicates a phosphate linkage. A subscript "f" indicates a 2'-F modification. A subscript "m" indicates a 2'-OMe sugar modification. N represents any nucleobase.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a long non-coding RNA. In certain embodiments, the target nucleic acid is a FXN transcript. In certain embodiments, the target RNA has the sequence set forth in SEQ ID NO. 1.

Friedreich's ataxia is caused by an expanded GAA repeat within intron 1 of the frataxin (FXN) gene that reduces expression of the FXN protein. Agents that increase expression of FXN protein have the potential to alleviate the disease.

Certain embodiments disclosed herein are drawn to a method of increasing expression of FXN in a cell comprising contacting the cell with an antisense compound targeted to the GAA repeat of FXN. In several aspects, FXN comprises a nucleic acid sequence at least 85% identical to SEQ ID NO:1.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other unmodified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1 Effect on Frataxin mRNA Expression of Compounds Targeting the GAA Repeat in Patient Cells by Electroporation Modified Oligonucleotides and Morpholinos The compounds in the following table were synthesized using standard methods well known in the art. The compounds target the GAA repeat region of the frataxin (FXN) gene.

Compounds 894618-894641 are modified oligonucleotides with full phosphorothioate backbones and 2' sugar chemistry as indicated in the table below. Compounds 894642-894644 are phosphoramidite morpholinos with a 5'-terminal conjugate as shown below:

The phosphoramidite morpholinos have the structure shown below (where Bx represents a modified or unmodified nucleobase). The structure below depicts two phosphoramidite morpholinos linked via a phosphoamidite linkage.

TABLE 1

Modified Oligonucleotides and Morpholinos

| Compound ID | 5' end | Chemistry Notation | SEQ ID No. |
|---|---|---|---|
| 894618 | H | $^mC_{es}T_{es}T_{es}\,^mC_{es}T_{es}T_{es}\,^mC_{es}T_{es}T_{es}\,^mC_{es}T_{es}T_{es}\,^mC_{es}T_{es}T_{es}\,^mC_e$ | 2 |
| 894619 | H | $T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_{es}T_e$ | 3 |
| 894620 | H | $T_{es}T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_e$ | 4 |
| 894621 | H | $^mC_{es}T_{ds}T_{ds}\,^mC_{es}T_{ds}T_{ds}\,^mC_{es}T_{ds}T_{ds}\,^mC_{es}T_{ds}T_{ds}\,^mC_{es}T_{ds}T_{ds}\,^mC_e$ | 2 |
| 894622 | H | $T_{es}\,^mC_{ds}T_{ds}T_{es}\,^mC_{ds}T_{ds}T_{es}\,^mC_{ds}T_{ds}T_{es}\,^mC_{ds}T_{ds}T_{es}\,^mC_{ds}T_{ds}T_e$ | 3 |
| 894623 | H | $T_{es}T_{ds}\,^mC_{ds}T_{es}T_{ds}\,^mC_{ds}T_{es}T_{ds}\,^mC_{ds}T_{es}T_{ds}\,^mC_{ds}T_{es}T_{ds}\,^mC_{ds}T_e$ | 4 |
| 894624 | H | $^mC_{ks}T_{ds}T_{ds}\,^mC_{ks}T_{ds}T_{ds}\,^mC_{ks}T_{ds}T_{ds}\,^mC_{ks}T_{ds}T_{ds}\,^mC_{ks}T_{ds}T_{ds}\,^mC_k$ | 2 |
| 894625 | H | $T_{ks}\,^mC_{ds}T_{ds}T_{ks}\,^mC_{ds}T_{ds}T_{ks}\,^mC_{ds}T_{ds}T_{ks}\,^mC_{ds}T_{ds}T_{ks}\,^mC_{ds}T_{ds}T_k$ | 3 |
| 894626 | H | $T_{ks}T_{ds}\,^mC_{ds}T_{ks}T_{ds}\,^mC_{ds}T_{ks}T_{ds}\,^mC_{ds}T_{ks}T_{ds}\,^mC_{ds}T_{ks}T_{ds}\,^mC_{ds}T_k$ | 4 |
| 894627 | H | $^mC_{ks}T_{es}T_{es}\,^mC_{ks}T_{es}T_{es}\,^mC_{ks}T_{es}T_{es}\,^mC_{ks}T_{es}T_{es}\,^mC_{ks}T_{es}T_{es}\,^mC_k$ | 2 |
| 894628 | H | $T_{ks}\,^mC_{es}T_{es}T_{ks}\,^mC_{es}T_{es}T_{ks}\,^mC_{es}T_{es}T_{ks}\,^mC_{es}T_{es}T_{ks}\,^mC_{es}T_{es}T_k$ | 3 |
| 894629 | H | $T_{ks}T_{es}\,^mC_{es}T_{ks}T_{es}\,^mC_{es}T_{ks}T_{es}\,^mC_{es}T_{ks}T_{es}\,^mC_{es}T_{ks}T_{es}\,^mC_{es}T_k$ | 4 |
| 894630 | H | $T_{es}T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_{es}\,^mC_e$ | 5 |
| 894631 | H | $^mC_{es}T_{es}T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_{es}T_e$ | 6 |
| 894632 | H | $T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_{es}T_{es}\,^mC_{es}T_e$ | 7 |
| 894633 | H | $T_{es}T_{es}\,^mC_{ds}T_{ds}T_{es}\,^mC_{ds}T_{ds}T_{es}\,^mC_{ds}T_{ds}T_{es}\,^mC_{ds}T_{ds}T_{es}\,^mC_{ds}T_{ds}T_{es}\,^mC_e$ | 5 |
| 894634 | H | $^mC_{es}T_{es}T_{ds}\,^mC_{ds}T_{es}T_{ds}\,^mC_{ds}T_{es}T_{ds}\,^mC_{ds}T_{es}T_{ds}\,^mC_{ds}T_{es}T_{ds}\,^mC_{ds}T_{es}T_e$ | 6 |
| 894635 | H | $T_{es}\,^mC_{es}T_{ds}T_{ds}\,^mC_{es}T_{ds}T_{ds}\,^mC_{es}T_{ds}T_{ds}\,^mC_{es}T_{ds}T_{ds}\,^mC_{es}T_{ds}T_{ds}\,^mC_{es}T_e$ | 7 |
| 894636 | H | $T_{ks}T_{ks}\,^mC_{ds}T_{ds}T_{ks}\,^mC_{ds}T_{ds}T_{ks}\,^mC_{ds}T_{ds}T_{ks}\,^mC_{ds}T_{ds}T_{ks}\,^mC_{ds}T_{ds}T_{ks}\,^mC_k$ | 5 |
| 894637 | H | $^mC_{ks}T_{ks}T_{ds}\,^mC_{ds}T_{ks}T_{ds}\,^mC_{ds}T_{ks}T_{ds}\,^mC_{ds}T_{ks}T_{ds}\,^mC_{ds}T_{ks}T_{ds}\,^mC_{ds}T_{ks}T_k$ | 6 |
| 894638 | H | $T_{ks}\,^mC_{ks}T_{ds}T_{ds}\,^mC_{ks}T_{ds}T_{ds}\,^mC_{ks}T_{ds}T_{ds}\,^mC_{ks}T_{ds}T_{ds}\,^mC_{ks}T_{ds}T_{ds}\,^mC_{ks}T_k$ | 7 |

TABLE 1-continued

Modified Oligonucleotides and Morpholinos

| Compound ID | 5' end | Chemistry Notation | SEQ ID No. |
|---|---|---|---|
| 894639 | H | $T_{ks}T_{ks}{}^mC_{es}T_{es}T_{ks}{}^mC_{es}T_{es}T_{ks}$ ${}^mC_{es}T_{es}T_{ks}{}^mC_{es}T_{es}T_{ks}{}^mC_{es}T_{es}$ $T_{ks}{}^mC_k$ | 5 |
| 894640 | H | ${}^mC_{ks}T_{ks}T_{es}{}^mC_{es}T_{ks}T_{es}{}^mC_{es}T_{ks}$ $T_{es}{}^mC_{es}T_{ks}T_{es}{}^mC_{es}T_{ks}T_{es}{}^mC_{es}$ $T_{ks}T_k$ | 6 |
| 894641 | H | $T_{ks}{}^mC_{ks}T_{es}T_{es}{}^mC_{ks}T_{es}T_{es}{}^mC_{ks}$ $T_{es}T_{es}{}^mC_{ks}T_{es}T_{es}{}^mC_{ks}T_{es}T_{es}$ ${}^mC_{ks}T_k$ | 7 |
| 894642 | shown above | TCTTCTTCTTCTTCTTCTTC (PMO) | 8 |
| 894643 | shown above | TTCTTCTTCTTCTTCTTCTT (PMO) | 9 |
| 894644 | shown above | CTTCTTCTTCTTCTTCTTCT (PMO) | 10 |
| 894645 | phosphate | $T_{es}U_{fs}U_{mo}C_{fs}U_{mo}U_{fs}C_{mo}U_{fs}A_{mo}$ $A_{fs}A_{mo}U_{fs}C_{mo}U_{fs}U_{ms}C_{fs}U_{ms}U_{fs}$ $C_{ms}A_{es}A_e$ | 11 |
| 894646 | phosphate | $T_{es}C_{fs}U_{mo}U_{fs}C_{mo}U_{fs}U_{mo}C_{fs}A_{mo}$ $A_{fs}A_{mo}U_{fs}U_{mo}C_{fs}U_{ms}U_{fs}C_{ms}U_{fs}$ $U_{ms}A_{es}A_e$ | 12 |
| 894647 | phosphate | $T_{es}U_{fs}C_{mo}U_{fs}U_{mo}C_{fs}U_{mo}U_{fs}A_{mo}$ $A_{fs}A_{mo}C_{fs}U_{mo}U_{fs}C_{ms}U_{fs}U_{ms}C_{fs}$ $U_{ms}A_{es}A_e$ | 13 |

A subscript "d" indicates an unmodified, 2'-deoxy sugar moiety. A subscript "e" indicates a 2'-methoxyethyl modification. A subscript "k" indicates a cEt modification. A subscript "s" indicates a phosphorothioate internucleoside linkage, while a subscript "o" indicates a phosphate linkage. A subscript "f" indicates a 2'-F modification. A subscript "m" indicates a 2'-OMe sugar modification. A superscript "m" indicates 5'-methyl Cytosine.

Experimental Protocol and Results

Frataxin patient fibroblasts (GM03816, 330/380 repeats) were cultured at 20,000 cells per well and transfected by electroporation at 140V with various concentrations of modified oligonucleotide as indicated in the table below. After approximately 24 hours, RNA was isolated from the cells and FXN mRNA levels were measured by quantitative real-time PCR. Human Sybr green PCR kit (forward sequence AAGCCATACACGTTTGAGGACTA, designated herein as SEQ ID NO: 17; reverse sequence TTGGCGTCTGCTTGTTGATCA, designated herein as SEQ ID NO: 18; was used to measure mRNA levels. FXN mRNA levels were normalized to total RNA content, as measured by RIBOGREEN®. Results are presented in the tables below as normalized FXN mRNA level, relative to untreated control cells (these conditions describe a "Standard Cell Assay"). Compound 582468 is a 5-10-5 MOE/DNA gapmer with the sequence GCCAATATCATAACCCAAGC (SEQ ID NO: 19), complementary to alpha 1 actin, and was included as a control.

TABLE 2

Effect of modified oligonucleotides and morpholinos on frataxin expression in patient fibroblasts

| | | Fold-increase Frataxin Expression | | | | | | |
|---|---|---|---|---|---|---|---|---|
| Compound ID | sugar motif | 0 μM | 0.625 μM | 1.25 μM | 2.5 μM | 5 μM | 10 μM | 20 μM |
| 894618 | e16 | 1.0 | 0.9 | 1.1 | 1.2 | 1.5 | 5.5 | 11.8 |
| 894619 | e16 | 1.0 | 0.9 | 1.0 | 1.2 | 1.1 | 2.6 | 5.7 |
| 894620 | e16 | 1.0 | 0.8 | 1.0 | 1.0 | 1.0 | 1.6 | 8.1 |
| 894621 | (edd)5-e | 1.0 | 0.8 | 1.1 | 0.9 | 1.0 | 0.8 | 0.9 |
| 894622 | (edd)5-e | 1.0 | 0.9 | 0.9 | 0.8 | 1.1 | 0.9 | 0.9 |
| 894623 | (edd)5-e | 1.0 | 1.0 | 0.9 | 0.9 | 1.0 | 0.8 | 0.9 |
| 894624 | (kdd)5-k | 1.0 | 1.0 | 0.9 | 0.8 | 0.8 | 1.0 | 2.4 |
| 894625 | (kdd)5-k | 1.0 | 0.9 | 0.9 | 0.8 | 0.9 | 1.5 | 8.9 |
| 894626 | (kdd)5-k | 1.0 | 0.8 | 0.9 | 0.9 | 0.8 | 1.1 | 4.1 |
| 894627 | (kee)5-k | 1.0 | 1.0 | 0.9 | 0.9 | 1.1 | 1.5 | 3.0 |
| 894628 | (kee)5-k | 1.0 | 0.9 | 1.2 | 1.0 | 1.1 | 1.5 | 2.2 |
| 582468 | e5-d10-e5 | 1.0 | 0.9 | 0.9 | 0.9 | 0.9 | 0.9 | 1.1 |
| 894629 | (kee)5-k | 1.0 | 0.8 | 0.8 | 0.6 | 0.7 | 1.2 | 2.0 |
| 894630 | e18 | 1.0 | 0.9 | 1.0 | 1.2 | 1.2 | 1.6 | 9.5 |
| 894631 | e18 | 1.0 | 0.9 | 0.9 | 1.2 | 1.3 | 2.9 | 16.9 |
| 894632 | e18 | 1.0 | 1.0 | 1.0 | 1.1 | 0.9 | 1.5 | 6.3 |
| 894633 | e-(edd)5-ee | 1.0 | 0.8 | 0.8 | 0.9 | 1.0 | 0.8 | 0.6 |
| 894634 | e-(edd)5-ee | 1.0 | 1.1 | 0.8 | 1.0 | 1.0 | 0.8 | 0.7 |
| 894635 | e-(edd)5-ee | 1.0 | 0.8 | 1.1 | 1.0 | 0.7 | 0.9 | 0.8 |
| 894636 | k-(kdd)5-kk | 1.0 | 0.8 | 1.0 | 1.1 | 0.8 | 2.6 | 9.9 |
| 894637 | k-(kdd)5-kk | 1.0 | 0.9 | 0.9 | 1.0 | 0.8 | 1.1 | 4.6 |
| 894638 | k-(kdd)5-kk | 1.0 | 0.9 | 0.8 | 1.0 | 0.9 | 1.5 | 8.4 |
| 894639 | k-(kee)5-kk | 1.0 | 1.0 | 1.0 | 1.2 | 1.1 | 1.2 | 1.4 |
| 582468 | e5-d10-e5 | 1.0 | 0.7 | 0.8 | 0.8 | 0.7 | 0.9 | 0.8 |
| 894640 | k-(kee)5-kk | 1.0 | 0.9 | 1.1 | 1.1 | 1.3 | 1.0 | 1.7 |
| 894641 | k-(kee)5-kk | 1.0 | 1.0 | 0.8 | 1.4 | 1.1 | 1.4 | 1.1 |
| 894642 | PMO | 1.0 | 1.2 | 1.0 | 1.3 | 1.3 | 1.0 | 0.6 |
| 894643 | PMO | 1.0 | 1.6 | 1.2 | 1.3 | 0.9 | 1.1 | 0.7 |
| 894644 | PMO | 1.0 | 1.2 | 1.1 | 1.4 | 0.7 | 1.0 | 0.6 |
| 894645 | e-(fm)9-ee | 1.0 | 1.4 | 1.2 | 1.3 | 1.2 | 1.3 | 1.3 |
| 894646 | e-(fm)9-ee | 1.0 | 1.4 | 1.0 | 1.4 | 1.3 | 1.2 | 1.1 |
| 894647 | e-(fm)9-ee | 1.0 | 1.2 | 1.1 | 1.4 | 1.3 | 1.2 | 1.0 |
| 582468 | e5-d10-e5 | 1.0 | 1.3 | 1.1 | 1.1 | 1.4 | 1.2 | 0.8 |

Example 2 Effect on Frataxin mRNA and Protein Expression of Compounds Targeting the GAA Repeat in Patient Cells by Lipid Transfection Selected modified oligonucleotides described in Example 1 above were further tested for their ability to increase frataxin protein expression in patient fibroblasts.

Frataxin patient fibroblasts (GM03816, 330/380 repeats) were cultured and transfected using lipofectamine with various concentrations of modified oligonucleotide. After approximately 96 hours, protein expression was measured by western blot. For the western blot, the primary antibody was anti-frataxin 4F9 (Dr. Helene Puccio at IGBMC, France) or was anti-frataxin ab110328 (Abcam) and the secondary antibody was HRP-anti-mouse (715-035-150, Jackson Laboratories). Protein bands were visualized using SuperSignal West Pico Chemiluminescent Substrate (Thermo Scientific), and bands were quantified using ImageJ. EC50 values were determined using GraphPad Prism 7.03.

TABLE 3

Effect of modified oligonucleotides on
frataxin protein expression in patient fibroblasts

| Compound ID | 0 nM | 1.56 nM | 3.13 nM | 6.25 nM | 12.5 nM | 25 nM | EC50 (nM) |
|---|---|---|---|---|---|---|---|
| | | | Relative Frataxin Protein Levels | | | | |
| 894618 | 1.0 | 1.7 | 1.8 | 1.9 | 3.1 | 2.6 | 4.4 |
| 894631 | 1.0 | 2 | 2.5 | 2.5 | 3.0 | 3.0 | 2.0 |
| 894622 | 1.0 | 1.4 | 2.2 | 2.7 | 3.4 | 3.2 | 3.2 |
| 894626 | 1.0 | 1.8 | 2.4 | 3.6 | 6.0 | 5.9 | 6.0 |
| 894627 | 1.0 | n.d. | 3.0 | 5.1 | 5.0 | 3.9 | 3.1 |
| 894639 | 1.0 | n.d. | 3.1 | 4.8 | 6.4 | 6.8 | 4.6 |
| 894640 | 1.0 | 2.3 | 2.9 | 4.0 | 3.3 | 3.3 | 1.6 |

Example 3 Effect on Frataxin mRNA and Protein Expression of ss-siRNA

Design and Synthesis of ss-siRNAs for Activation of Frataxin Expression

The compounds in the following table were synthesized using standard methods well known in the art. Examples of synthesis can be found, for example, in WO 2011/139702, which is hereby incorporated by reference in its entirety. The compounds in the table below are designed target the GAA repeat region of the frataxin (FXN) gene.

TABLE 4

Modified Oligonucleotides

| Compound ID | 5' end | Chemistry Notation (5'-3') | SEQ ID No. |
|---|---|---|---|
| 1188749 | P | P-T$_{es}$U$_{fs}$U$_m$C$_{fs}$U$_m$U$_{fs}$C$_m$U$_{fs}$U$_m$C$_{fs}$U$_m$U$_{fs}$C$_m$U$_{fs}$U$_{ms}$C$_{fs}$U$_{ms}$U$_{fs}$C$_{ms}$A$_{es}$A$_e$ | 14 |
| 1188751 | P | P-T$_{es}$C$_{fs}$U$_m$C$_{fs}$U$_m$U$_{fs}$C$_m$U$_{fs}$U$_m$C$_{fs}$U$_m$U$_{fs}$C$_m$U$_{fs}$U$_m$C$_{fs}$U$_{ms}$U$_{fs}$C$_m$U$_{fs}$U$_{ms}$A$_{es}$A$_e$ | 15 |
| 1188754 | P | P-T$_{es}$U$_{fs}$C$_m$U$_{fs}$U$_m$C$_{fs}$U$_m$U$_{fs}$C$_m$U$_{fs}$U$_m$C$_{fs}$U$_{ms}$U$_{fs}$C$_m$U$_{fs}$U$_{ms}$A$_{es}$A$_e$ | 16 |
| 1204706 | Pv | PV-T$_{es}$U$_{fs}$U$_m$C$_{fs}$U$_m$U$_{fs}$C$_m$U$_{fs}$U$_m$C$_{fs}$U$_m$U$_{fs}$C$_m$U$_{fs}$U$_{ms}$C$_{fs}$U$_{ms}$U$_{fs}$C$_{ms}$A$_{es}$A$_e$ | 14 |
| 1204707 | Pv | PV-T$_{es}$C$_{fs}$U$_m$U$_{fs}$C$_m$U$_{fs}$U$_m$C$_{fs}$U$_m$U$_{fs}$C$_m$U$_{fs}$U$_m$C$_{fs}$U$_{ms}$U$_{fs}$C$_m$U$_{fs}$U$_{ms}$A$_{es}$A$_e$ | 15 |
| 1204710 | Pv | PV-T$_{es}$U$_{fs}$C$_m$U$_{fs}$U$_m$C$_{fs}$U$_m$U$_{fs}$C$_m$U$_{fs}$U$_m$C$_{fs}$U$_{ms}$U$_{fs}$C$_m$U$_{fs}$U$_{ms}$A$_{es}$A$_e$ | 16 |

"P" at the 5'-end indicated a phosphate. "Pv" at the 5'-end indicates a 5'-(E)-vinylphosphonate group. The structure below represents an oligonucleotide with a 5'-(E)-vinylphosphonate group at the 5'-terminus. Bx represents a heterocyclic base moiety, X$_a$ represents a O or S, and R$_d$ represents a 2'-substitutent (e.g. 2'-MOE or 2'-OMe).

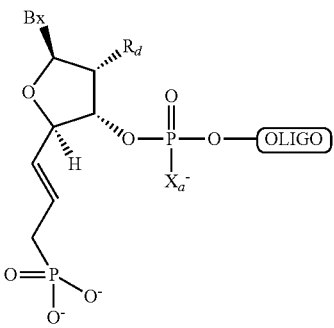

Activation of Expression of Frataxin mRNA and Protein in Patient-Derived Cells

Compounds described above were tested for their ability to activate frataxin expression in patient-derived GM03816 cells as described in Example 2 above. Table 5 represents data upon the treatment of GM03816 cells with 12.5 nM of modified oligonucleotide, while Table 6 represents a dose response.

TABLE 5

Effect of modified oligonucleotides on frataxin mRNA
and protein expression in patient fibroblasts

| Compound ID | Relative Levels of FXN mRNA | Relative Levels of FXN Protein |
|---|---|---|
| 1188749 | 1.67 | 2.44 |
| 1188751 | 1.59 | 2.79 |
| 1188754 | 2.07 | 2.85 |

TABLE 6

Dose response effect of modified oligonucleotides
on frataxin protein expression in patient fibroblasts

| Compound ID | 0 nM | 1.56 nM | 3.13 nM | 6.25 nM | 12.5 nM | 25 nM | EC50 (nM) |
|---|---|---|---|---|---|---|---|
| | | | Relative Frataxin Protein Levels | | | | |
| 1188749 | 1.0 | 1.5 | 1.6 | 3.2 | 3.6 | 4.4 | 5.0 |
| 1188751 | 1.0 | 1.9 | 1.9 | 2.1 | 2.2 | 3.1 | 6.2 |
| 1188754 | 1.0 | 1.7 | 2.0 | 1.5 | 2.6 | 2.9 | 3.2 |

The invention claimed is:

1. A method of treating, preventing, or ameliorating a disease associated with frataxin in an individual comprising administering to the individual a compound targeted to the repeat of frataxin thereby treating, preventing, or ameliorating the disease, wherein the compound comprises a modified oligonucleotide 16 to 80 linked nucleosides in length having a nucleobase sequence comprising at least 16 contiguous nucleobases of any of the nucleobase sequences of SEQ ID NOs: 2, 3, 4, 5, 6, 7, 8, 9, 10, 11, 12, 13, 14, 15 or 16 and wherein the compound comprises a sugar motif selected from the group consisting of e16, (edd)5-e, (kdd)5-k, (kee)5k, e18, e-(edd)5ee, k-(kdd)5kk, k-(kee)5-kk, and e-(fm)9-ee, where e represents a 2'-methoxyethyl modified nucleoside, d represents a 2'-deoxy nucleoside, k represents a 2'-cEt modified nucleoside, f represents a 2'F modified nucleoside and m represents a 2'OMe modified nucleoside.

2. The method of claim 1, wherein the disease is Friedreich's Ataxia.

3. The method of claim 1, wherein administering the compound inhibits, reduces, or improves the symptoms of Friedreich's Ataxia.

4. A method of increasing expression of frataxin in a cell comprising contacting the cell with a compound targeted to the GAA repeat of frataxin, thereby increasing expression of frataxin in the cell, wherein the compound comprises a modified oligonucleotide 16 to 80 linked nucleosides in length having a nucleobase sequence comprising at least 16 contiguous nucleobases of any of the nucleobase sequences of SEQ ID NOs: 2, 3, 4, 5, 6, 7, 8, 9, 10, 11, 12, 13, 14, 15 or 16 and wherein the compound comprises a sugar motif selected from the group consisting of e16, (edd)5-e, (kdd)5-k, (kee)5k, e18, e-(edd)5ee, k-(kdd)5kk, k-(kee)5-kk, and e-(fm)9-ee, where e represents a 2'-methoxyethyl modified nucleoside, d represents a 2'-deoxy nucleoside, k represents a 2'-cEt modified nucleoside, f represents a 2'F modified nucleoside and m represents a 2'OMe modified nucleoside.

5. The method of claim 4, wherein the cell is in the CNS of an individual.

6. The method of claim 5, wherein the individual has, or is at risk of having, Friedreich's ataxia.

7. The method of claim 1, wherein the compound is administered to the CNS of the individual.

8. The method of claim 1, wherein the modified oligonucleotide comprises at least one modified internucleoside linkage or at least one modified nucleobase.

9. The method of claim 8, wherein the modified internucleoside linkage is a phosphorothioate internucleoside linkage.

10. The method of claim 1, wherein the compound is single-stranded.

11. The method of claim 1, wherein the compound is double-stranded.

12. The method of claim 1, wherein the sugar motif is (edd)5-e, where e represents a 2'-methoxyethyl modified nucleoside and d represents a 2'-deoxy nucleoside.

13. The method of claim 1, wherein the sugar motif is (kdd)5-k, where k represents a 2'-cEt modified nucleoside and d represents a 2'-deoxy nucleoside.

14. The method of claim 1, wherein the sugar motif is (kee)5-k, where k represents a 2'-cEt modified nucleoside and e represents a 2'-methoxyethyl modified nucleoside.

15. The method of claim 1, wherein each internucleoside linkage is selected from phosphorothioate internucleoside linkage and phosphodiester internucleoside linkage.

16. The method of claim 1, wherein each internucleoside linkage is phosphorothioate.

17. The method of claim 8, wherein each sugar is a modified sugar.

18. The method of claim 17, wherein each modified sugar is a 2'-methoxyethyl sugar.

19. The method of claim 10, wherein the single-stranded oligonucleotide consists of 16 to 30 linked nucleosides having a nucleobase sequence complementary to a repeat region of an expanded repeat-containing target RNA, wherein the 5'-terminal nucleoside of the single-stranded oligonucleotide comprises a stabilized phosphate moiety and an internucleoside linking group linking the 5'-terminal nucleoside to the remainder of the single-stranded oligonucleotide.

20. The method of claim 19, wherein the single-stranded oligonucleotide has a nucleobase sequence comprising at least 16 contiguous nucleobases of any of the nucleobase sequences of SEQ ID NOs: 14, 15, or 16.

21. The method of claim 1, wherein the sugar motif is e-(edd)5-ee, where e represents a 2'-methoxyethyl modified nucleoside and d represents a 2'-deoxy nucleoside.

22. The method of claim 1, wherein the sugar motif is k-(kdd)5-kk, where k represents a 2'-cEt modified nucleoside and d represents a 2'-deoxy nucleoside.

23. The method of claim 1, wherein the sugar motif is k-(kee)5-kk, where k represents a 2'-cEt modified nucleoside and e represents a 2'-methoxyethyl modified nucleoside.

* * * * *